(12) United States Patent
Brown et al.

(10) Patent No.: US 12,290,482 B2
(45) Date of Patent: May 6, 2025

(54) ELEVATING WALKER CHAIR AND COMPONENTS

(71) Applicant: Exokinetics, Inc., West Chester, PA (US)

(72) Inventors: Garrett W. Brown, Philadelphia, PA (US); Ryan Christopher Meers, West Chester, PA (US); Daniel Richard Lefebvre, Philadelphia, PA (US); Stephan Michael Lawson, Malvern, PA (US)

(73) Assignee: EXOKINETICS, INC., West Chester, PA (US)

(*) Notice: Subject to any disclaimer, the term of this patent is extended or adjusted under 35 U.S.C. 154(b) by 396 days.

(21) Appl. No.: 17/174,157

(22) Filed: Feb. 11, 2021

(65) Prior Publication Data

US 2021/0205158 A1 Jul. 8, 2021

Related U.S. Application Data

(63) Continuation-in-part of application No. 16/982,365, filed as application No. PCT/US2019/023661 on
(Continued)

(51) Int. Cl.
*A61G 5/14* (2006.01)
*A61G 5/10* (2006.01)
*A61H 3/04* (2006.01)

(52) U.S. Cl.
CPC ............. *A61G 5/14* (2013.01); *A61G 5/1059* (2013.01); *A61H 3/04* (2013.01);
(Continued)

(58) Field of Classification Search
CPC ........... A61G 5/14; A61G 5/1059; A61H 3/04
See application file for complete search history.

(56) References Cited

U.S. PATENT DOCUMENTS 2,613,730 A * 10/1952 Anderson ................ A47C 4/10
297/42
4,211,426 A * 7/1980 Motloch ................ A47D 13/04
297/307
(Continued)

FOREIGN PATENT DOCUMENTS

CN 103717191 A 4/2014
GB 1406420 A 9/1975
(Continued)

OTHER PUBLICATIONS

First Notification of Examiner's Opinion issued on Feb. 14, 2022 in Chinese Patent Application 201980022937.X.
(Continued)

*Primary Examiner* — Philip F Gabler
(74) *Attorney, Agent, or Firm* — Barnes & Thornburg LLP

(57) ABSTRACT

A foldable, elevating walker chair is disclosed having a height adjustment mechanism and a height limiter. The elevating walker chair has a unique lifting mechanism that allows the chair to be readily raised and lowered without motors. The weight of the elevating walker chair may be optimized by use of innovative bracing struts. The folding mechanism allows the elevating walker chair to achieve a compact configuration. Innovative components such as a swivel seat, hinges, seatbelt, telescoping wheel mounts, height adjustment devices and safety mechanisms may be included in the elevating walker chair.

16 Claims, 41 Drawing Sheets

Related U.S. Application Data

Mar. 22, 2019, now Pat. No. 11,602,469, and a continuation-in-part of application No. 16/346,363, filed as application No. PCT/US2017/060163 on Nov. 6, 2017, now Pat. No. 11,685,188, said application No. 16/982,365 is a continuation-in-part of application No. 15/326,113, filed on Jan. 13, 2017, now Pat. No. 10,842,706.

(60) Provisional application No. 62/975,449, filed on Feb. 12, 2020, provisional application No. 62/649,809, filed on Mar. 29, 2018, provisional application No. 62/649,746, filed on Mar. 29, 2018, provisional application No. 62/420,383, filed on Nov. 10, 2016.

(52) U.S. Cl.
CPC ............... *A61H 2201/0192* (2013.01); *A61H 2201/1253* (2013.01); *A61H 2201/1418* (2013.01); *A61H 2201/1642* (2013.01); *A61H 2201/165* (2013.01); *A61H 2201/1671* (2013.01); *A61H 2201/1676* (2013.01); *A61H 2203/0431* (2013.01)

(56) References Cited

U.S. PATENT DOCUMENTS

| | | | | |
|---|---|---|---|---|
| 4,249,774 | A * | 2/1981 | Andreasson | A61G 5/14 297/316 |
| 4,824,170 | A * | 4/1989 | Goldmeier | A47C 3/18 297/130 |
| 5,316,370 | A | 5/1994 | Newman | |
| 5,673,970 | A * | 10/1997 | Holmquist | A47C 7/506 297/DIG. 10 |
| 5,984,411 | A * | 11/1999 | Galumbeck | A47C 9/005 297/DIG. 10 |
| 6,125,957 | A | 10/2000 | Kauffman | |
| 8,375,472 | B2 * | 2/2013 | Ashline | B60R 22/001 2/421 |
| 9,050,231 | B2 | 6/2015 | Masters | |
| 9,358,947 | B1 * | 6/2016 | Zorn | B60R 22/26 |
| 10,092,467 | B2 | 10/2018 | Mackert | |
| 10,327,553 | B2 | 6/2019 | Kiwak | |
| 10,682,271 | B2 | 6/2020 | Lin | |
| 10,888,169 | B1 | 1/2021 | Ma | |
| 11,602,469 | B2 | 3/2023 | Brown | |
| 2004/0226567 | A1 | 11/2004 | Klemm | |
| 2005/0017559 | A1 | 1/2005 | Kao | |
| 2005/0264070 | A1 * | 12/2005 | Kao | A61G 5/14 297/284.11 |
| 2007/0227787 | A1 | 10/2007 | Kuramoto | |
| 2010/0123346 | A1 * | 5/2010 | Lin | A47C 1/03 297/411.37 |
| 2010/0207354 | A1 | 8/2010 | Hunziker | |
| 2015/0075575 | A1 | 3/2015 | Karlovich | |
| 2016/0250095 | A1 | 9/2016 | Liu | |
| 2016/0287038 | A1 * | 10/2016 | Nelson | A47K 13/005 |
| 2016/0297327 | A1 * | 10/2016 | Adam | A47C 3/18 |
| 2016/0310334 | A1 | 10/2016 | Bliem | |
| 2017/0209319 | A1 | 7/2017 | Fawcett et al. | |
| 2021/0196047 | A1 | 7/2021 | Zhang | |

FOREIGN PATENT DOCUMENTS

| | | |
|---|---|---|
| JP | H10179644 A | 7/1998 |
| PL | 211202 B1 | 4/2012 |
| TW | 201941717 A | 11/2019 |
| WO | 2013006845 A2 | 1/2013 |

OTHER PUBLICATIONS

International Search Report and Written Opinion issued on Jun. 4, 2021 in PCT/US2021/017703.
Extended (Supplementary) European Search Report issued on Dec. 6, 2021 in European Patent Application 19825315.5.
Final Office Action dated Oct. 23, 2023; U.S. Appl. No. 18/182,863.

\* cited by examiner

Cross-section T-T

Cross-section R-R

SECTION F-F

DETAIL G

SECTION K-K

SECTION V-V

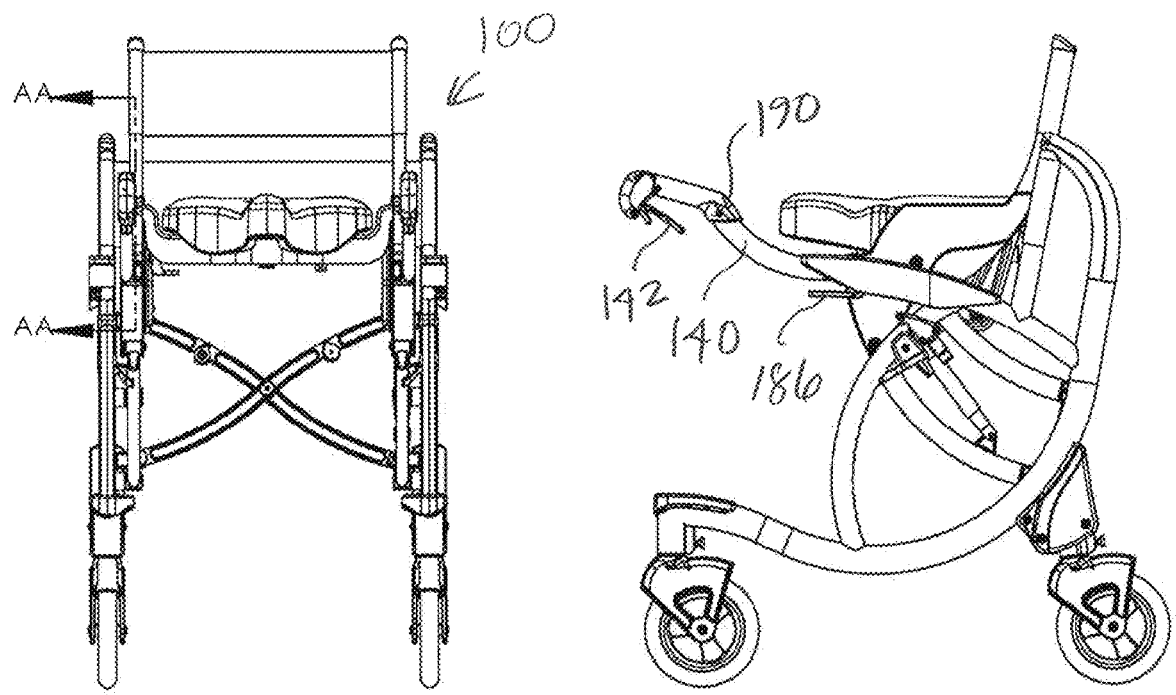
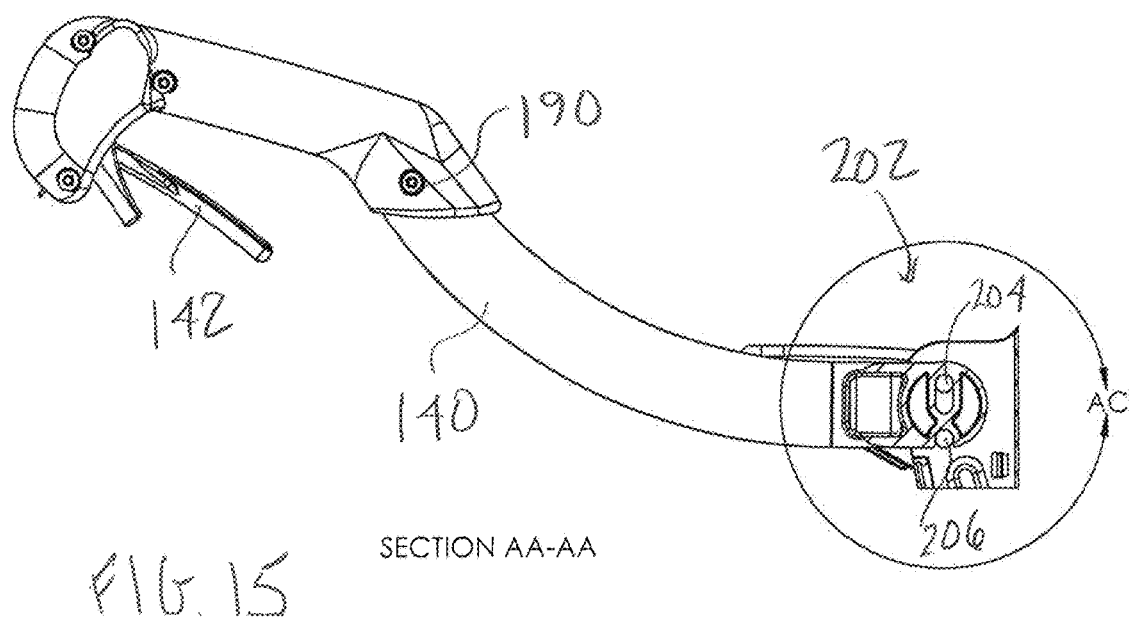
SECTION AA-AA
FIG. 15

SECTION AB-AB

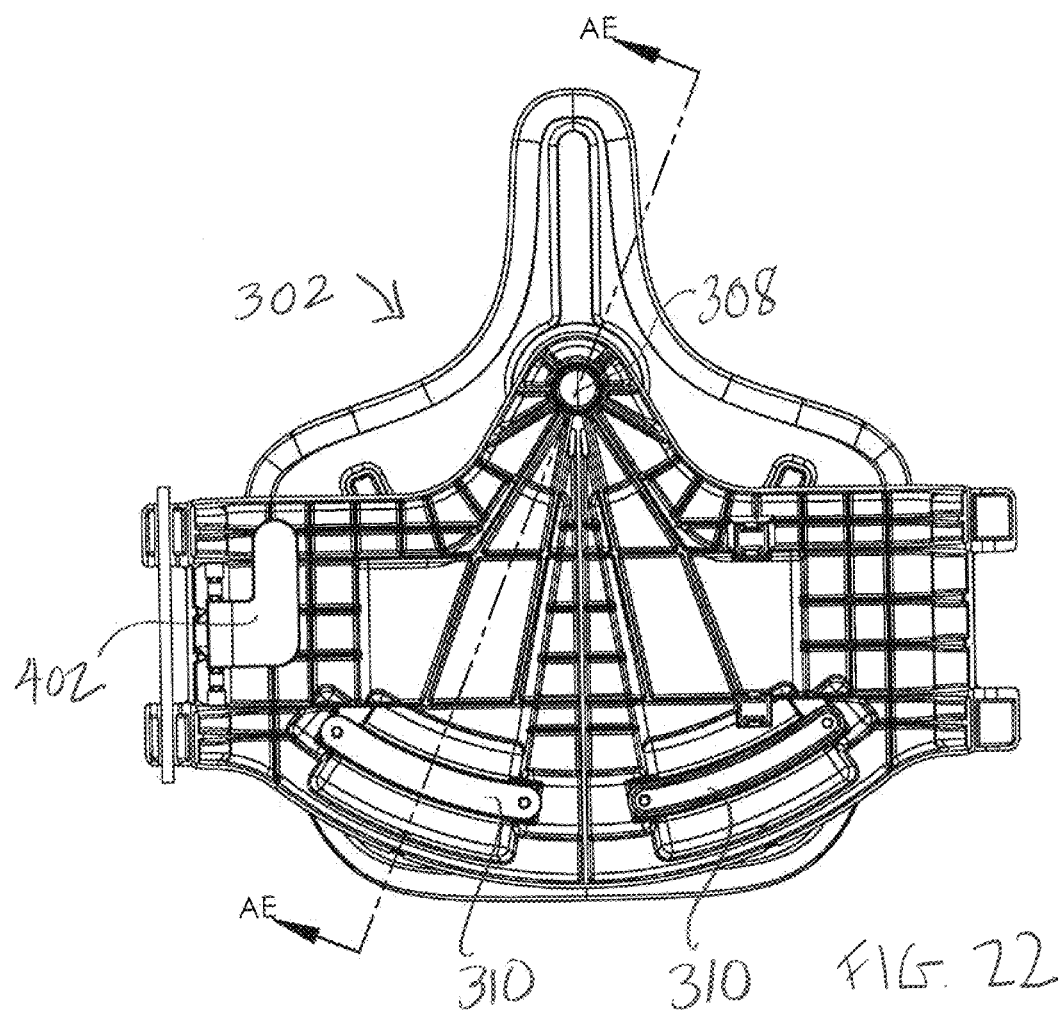
FIG. 22
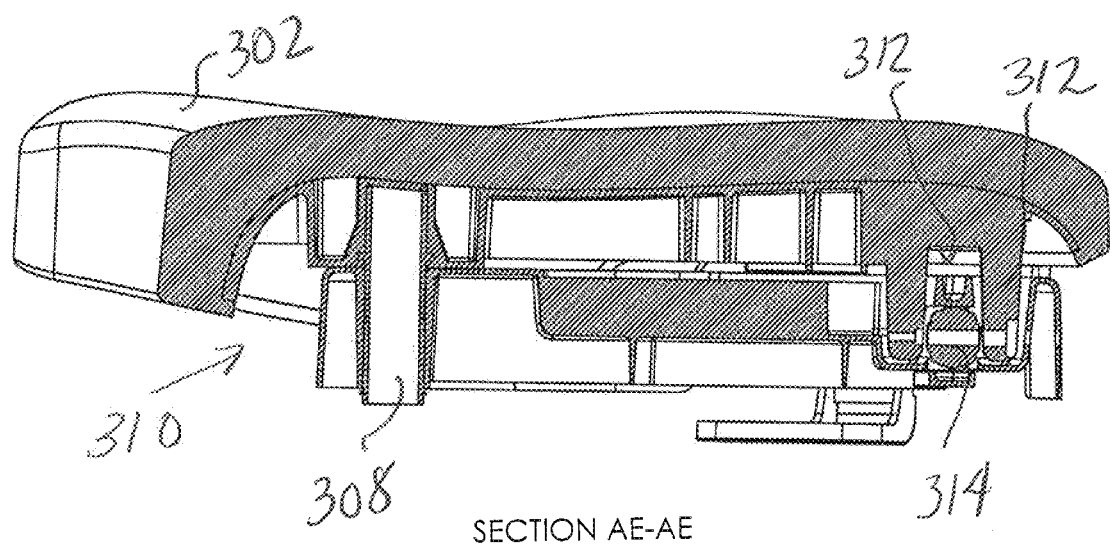
SECTION AE-AE

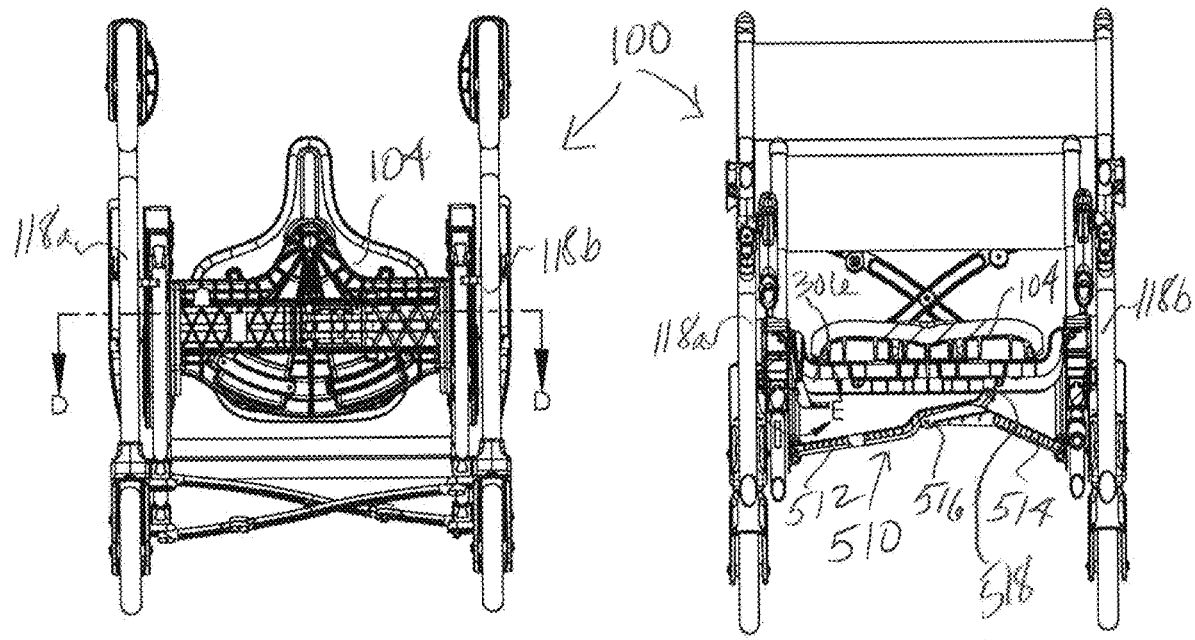
FIG. 24
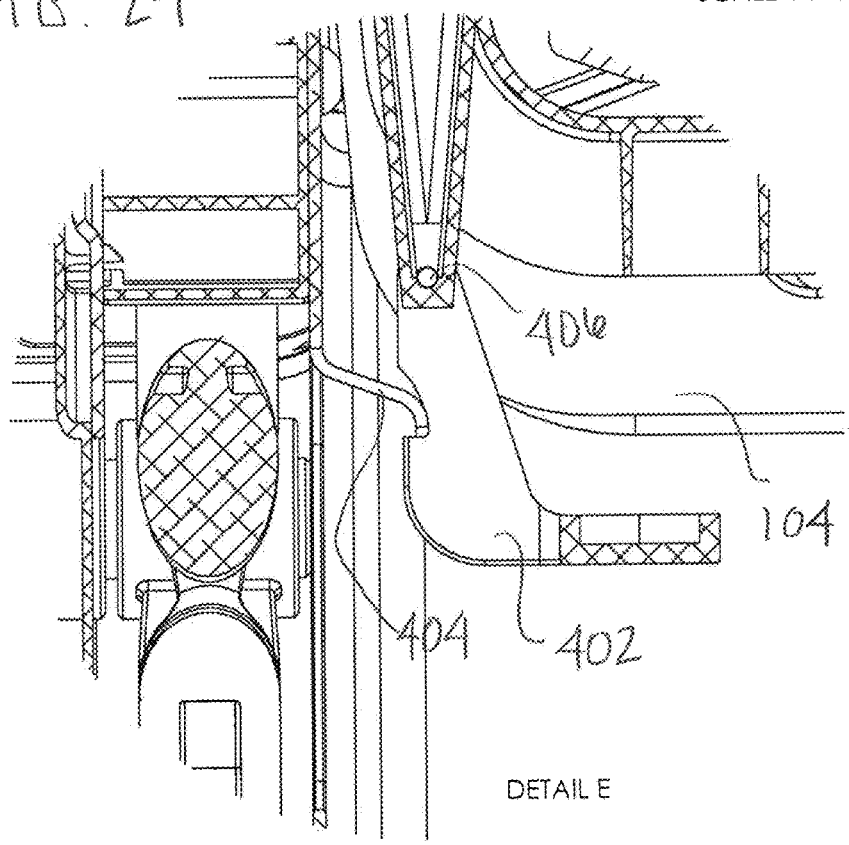
DETAIL E

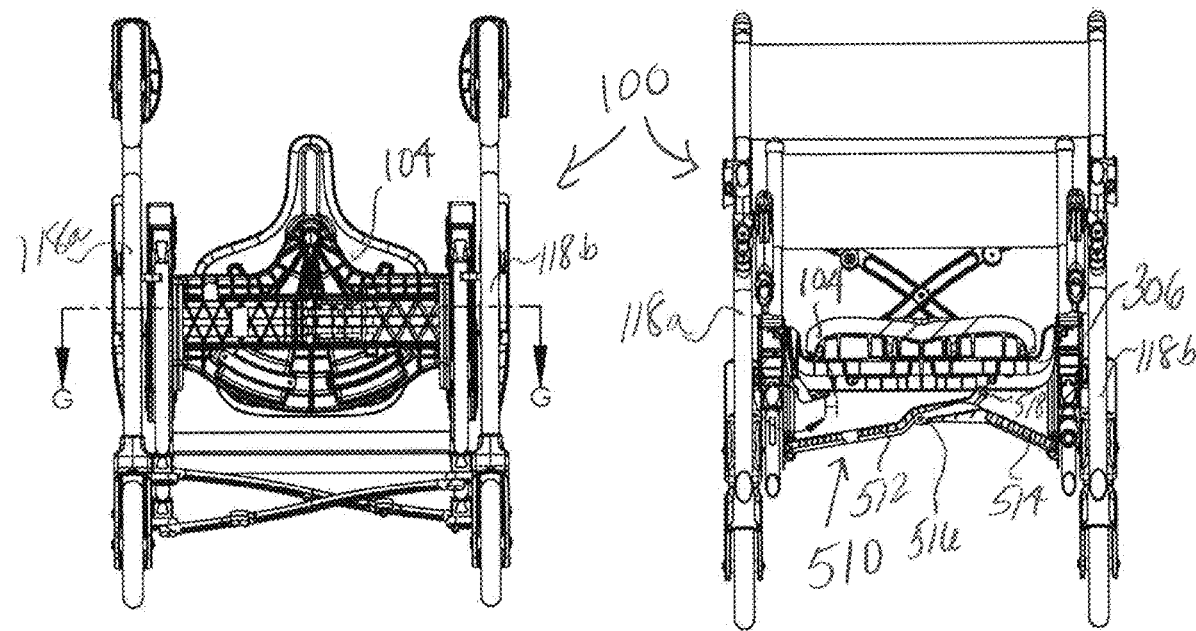
FIG. 25
SECTION G-G
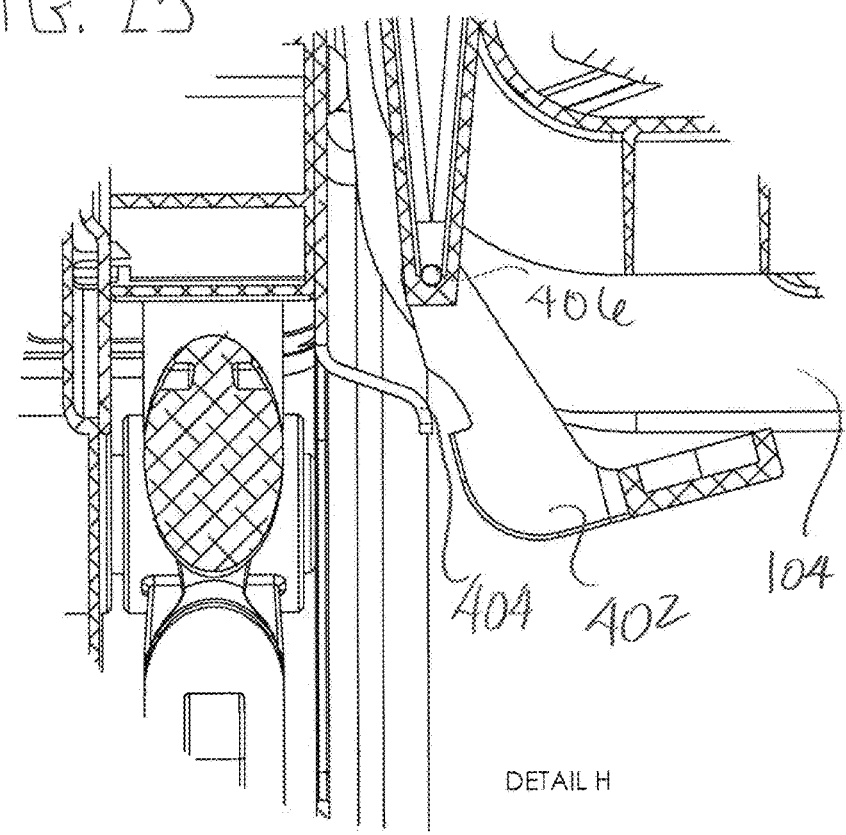
DETAIL H

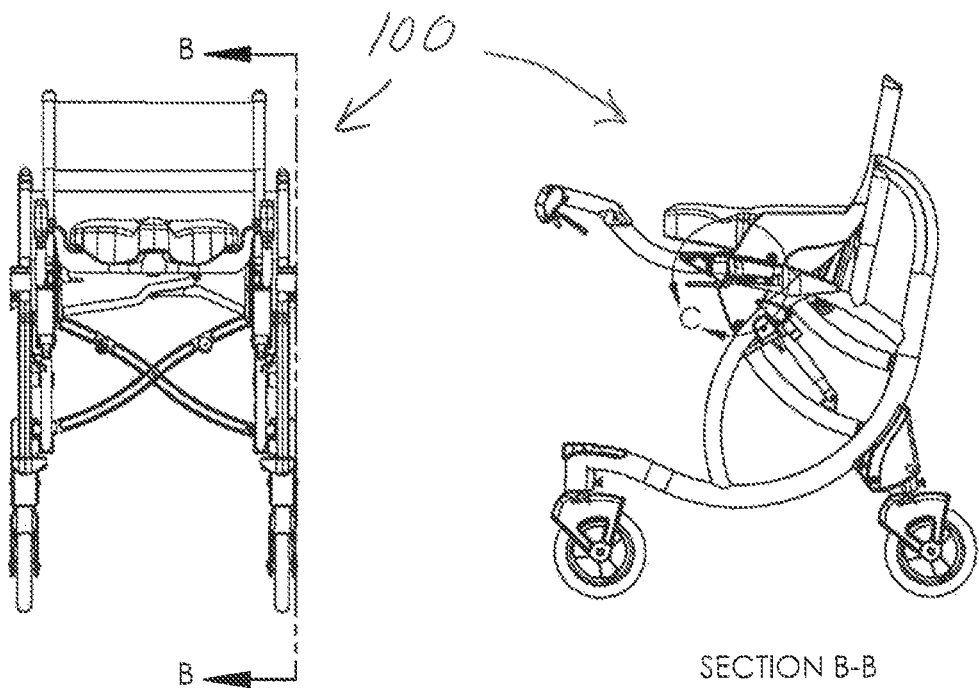
SECTION B-B
FIG. 37
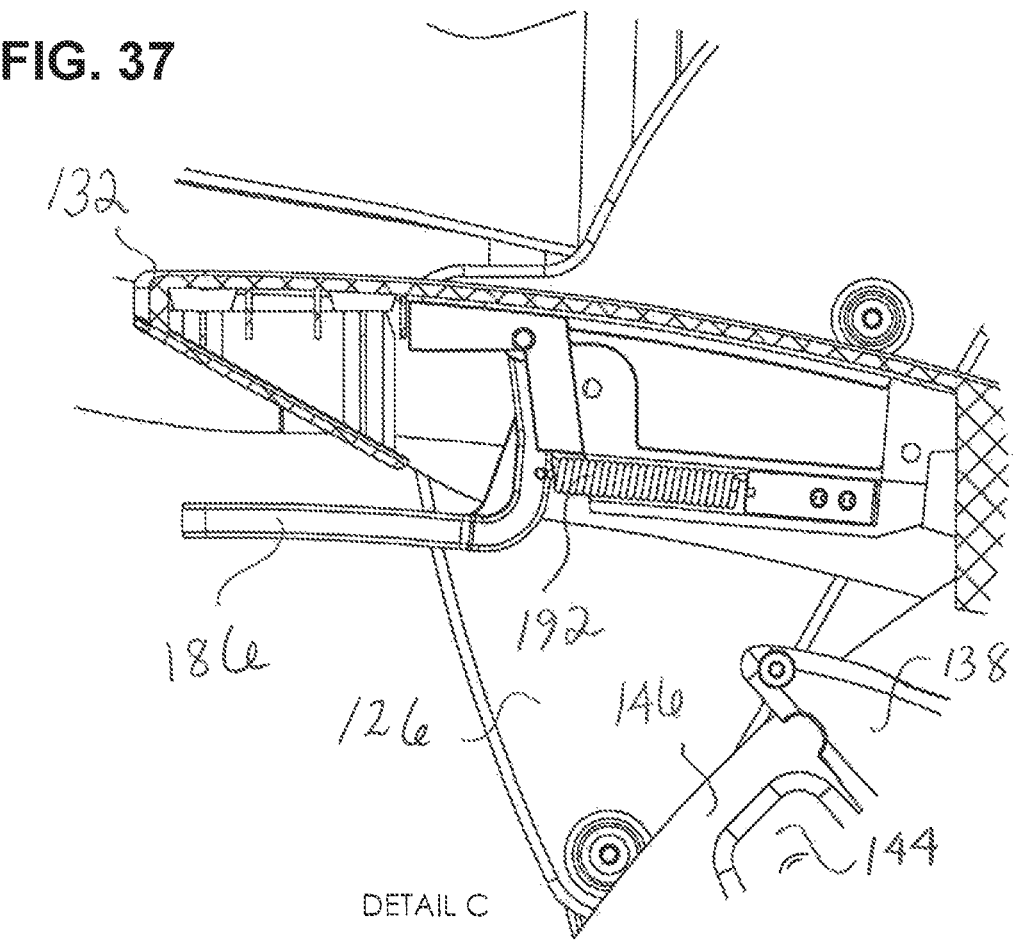
DETAIL C

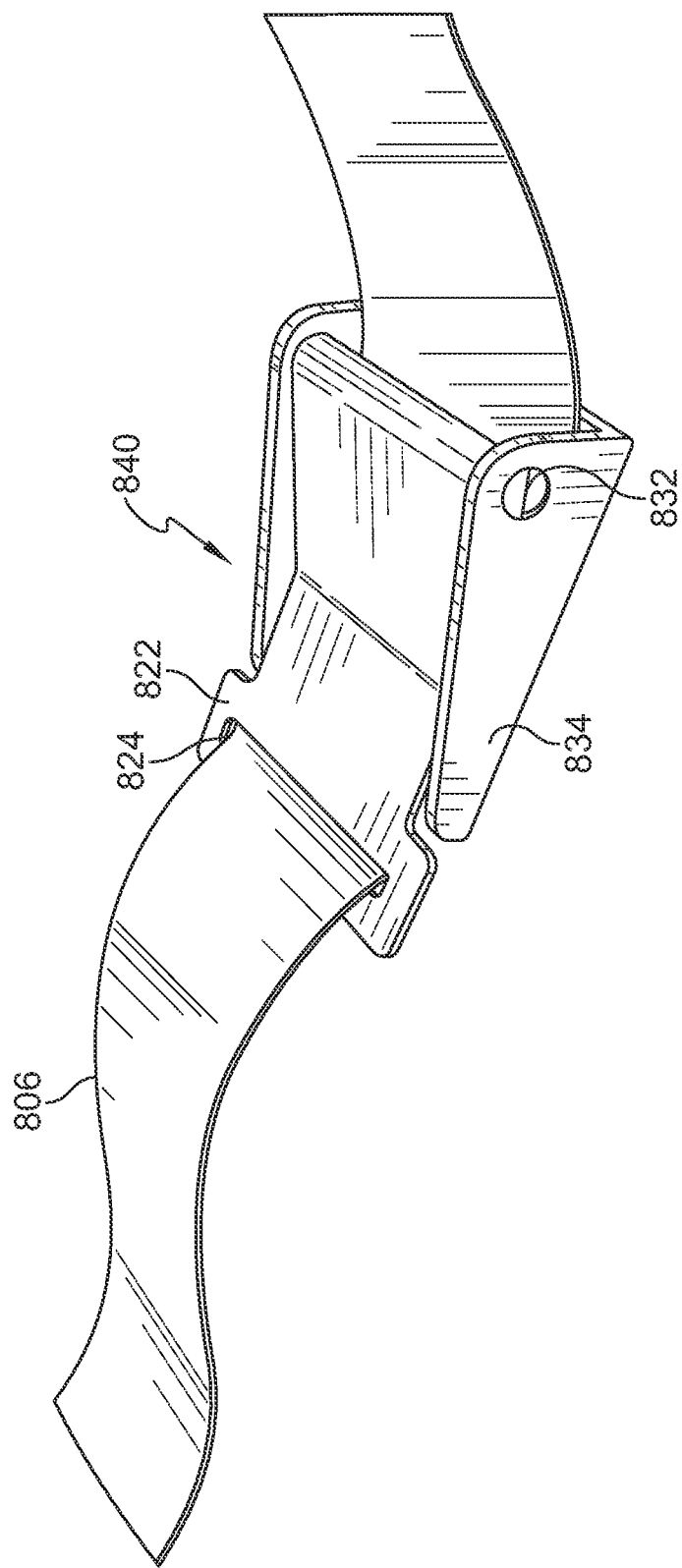

ELEVATING WALKER CHAIR AND COMPONENTS

BACKGROUND

Conventional devices to assist individuals having mobility difficulties fall into two broad categories—walkers and wheelchairs—plus several intermediate combinations that may additionally help occupants rise up and ambulate.

Conventional walker devices add support and stability but involve the user's hands and arms to an extent that precludes carrying or manipulating anything while moving. Four-wheeled walkers may also include seats, but they cannot be employed unless the user stops and turns around.

Walkers are slow and isolating, and inherently dangerous when set aside in order sit down.

Most non-powered and powered wheelchair users remain interminably seated, at the expense of muscular, circulatory, and cardiac well-being.

Elevating wheelchairs employ large motors to raise strapped-in occupants to a standing position and some can power them from place to place while upright, but without reinforcing ambulatory abilities or requiring any muscular contribution.

Another intermediary category of assistive devices includes 'stand-up' walkers, which partly lift occupants up and down and encourage them to walk.

Unfortunately, existing stand-up walkers inhibit user interactions with the world—either by having large structures ahead and rear entry, or with clumsily uncomfortable folding seats, procedures and restraints. And the users must still lift a significant percentage of body weight with legs and arms in order to rise from a seated to a standing position.

What is missing is a means for individuals with ambulatory limitations to sit and stand at will, to walk with a relatively natural gait, and to safely and easily interact with their environment—to cook, clean, do the wash, get dressed and transport themselves—all at the altitude desired, and with at least a small component of their own energy and former athleticism.

SUMMARY

A foldable, elevating walker chair is disclosed having a height adjustment mechanism and may include a height limiter. The elevating walker chair has a lifting mechanism that allows the chair's occupant to be readily raised and lowered without motors.

The weight of the elevating walker chair may be optimized by use of innovative bracing struts.

Telescoping wheel mounts may provide an increased height adjustment range.

A folding mechanism may be provided that allows the elevating walker chair to achieve a compact configuration. When folded, it may also be used as a walking support.

Innovative components such as a swivel seat, hinges, seatbelt, height adjustment and safety mechanisms may be included in the elevating walker chair.

DESCRIPTION OF THE DRAWINGS

All drawings are of illustrative embodiments of an elevating walker chair and its components. Various components may be shown that may be incorporated into various embodiments.

FIG. 15 depicts front and side views of an elevating walker chair having handle bars in an extended mode, and a close up, cross-sectional view of a handle bar pivot.

FIG. 22 is a view from the underside of a swivel seat and a cut-away cross-sectional view.

FIG. 24 depicts a bottom view and front view of an elevating walker chair, and a cross-sectional view of a seat release lever portion in a locked position.

FIG. 25 depicts a bottom view and front view of an elevating walker chair, and a cross-sectional view of a seat release lever portion in an unlocked position.

FIG. 37 depicts a cut-away of a seat height lock safety mechanism.

FIGS. 41A-C depict a cam buckle in an open position, closed positon and threaded with webbing.

DESCRIPTION OF THE INVENTION

The figures include some parts that are duplicated in the apparatuses shown, such as right and left components. Such parts may be identified individually by letters following the part number. For simplicity, a part number may be used without a letter, but may be intended to apply to multiple occurrences of the part.

Where reference numbers are followed by letters, "a" refers to a chair occupant's right side and "b" to a chair occupants left side. Where reference numbers are followed by letter a, b, c or d, "a" and "b" refer to the front of the apparatus and "c" and "d" refer to the rear of the apparatus, with "c" referring to a chair occupant's right side and "d" referring to a chair occupants left side. In some instances, particularly when only one of multiple components are shown, the letters may be omitted. It is noted that components may be mirror images of one another on opposing right and left sides.

Figure 1:
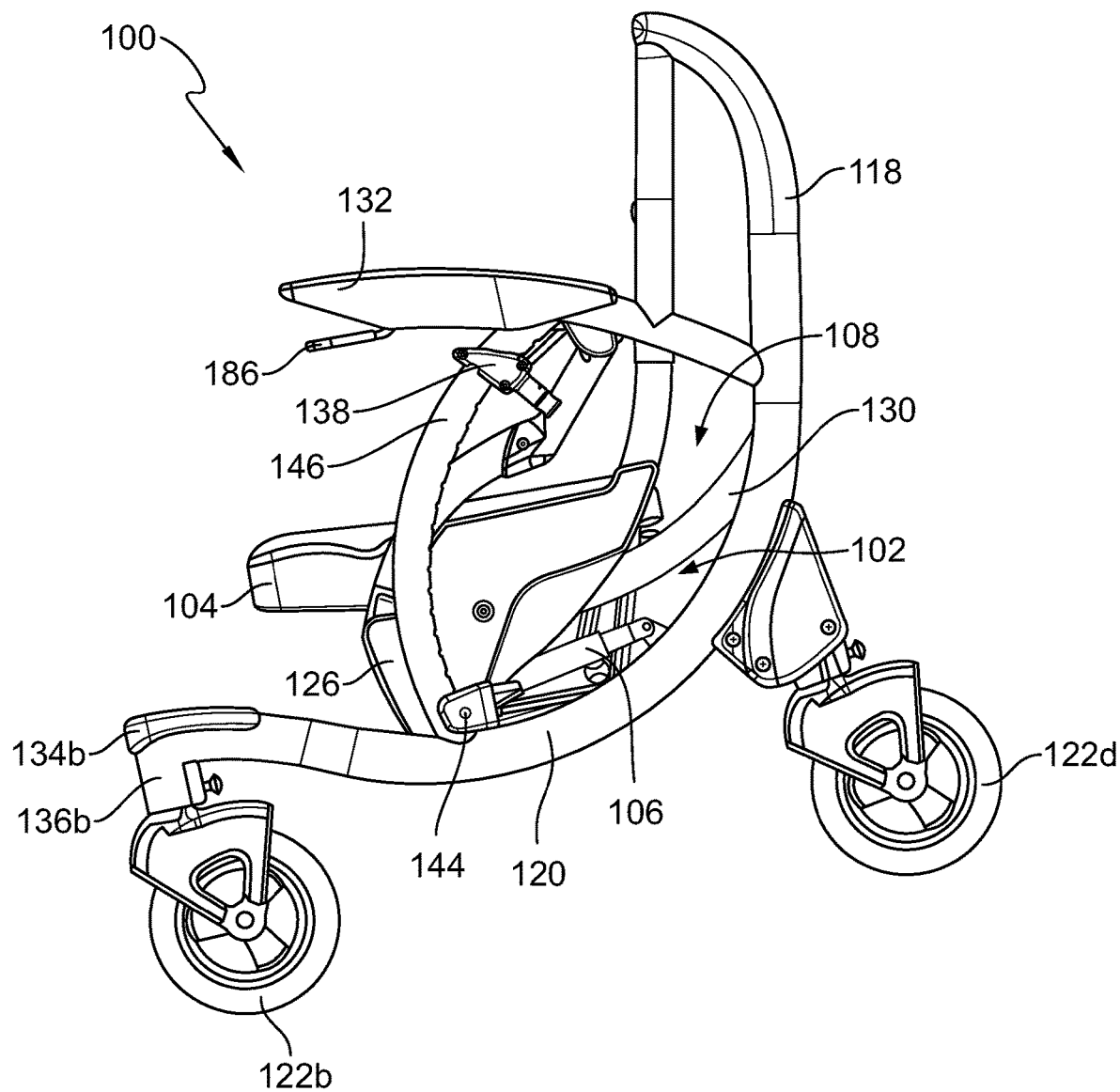
FIG. 1 depicts a side view of an elevating walker chair in a sitting mode.
Figure 2:
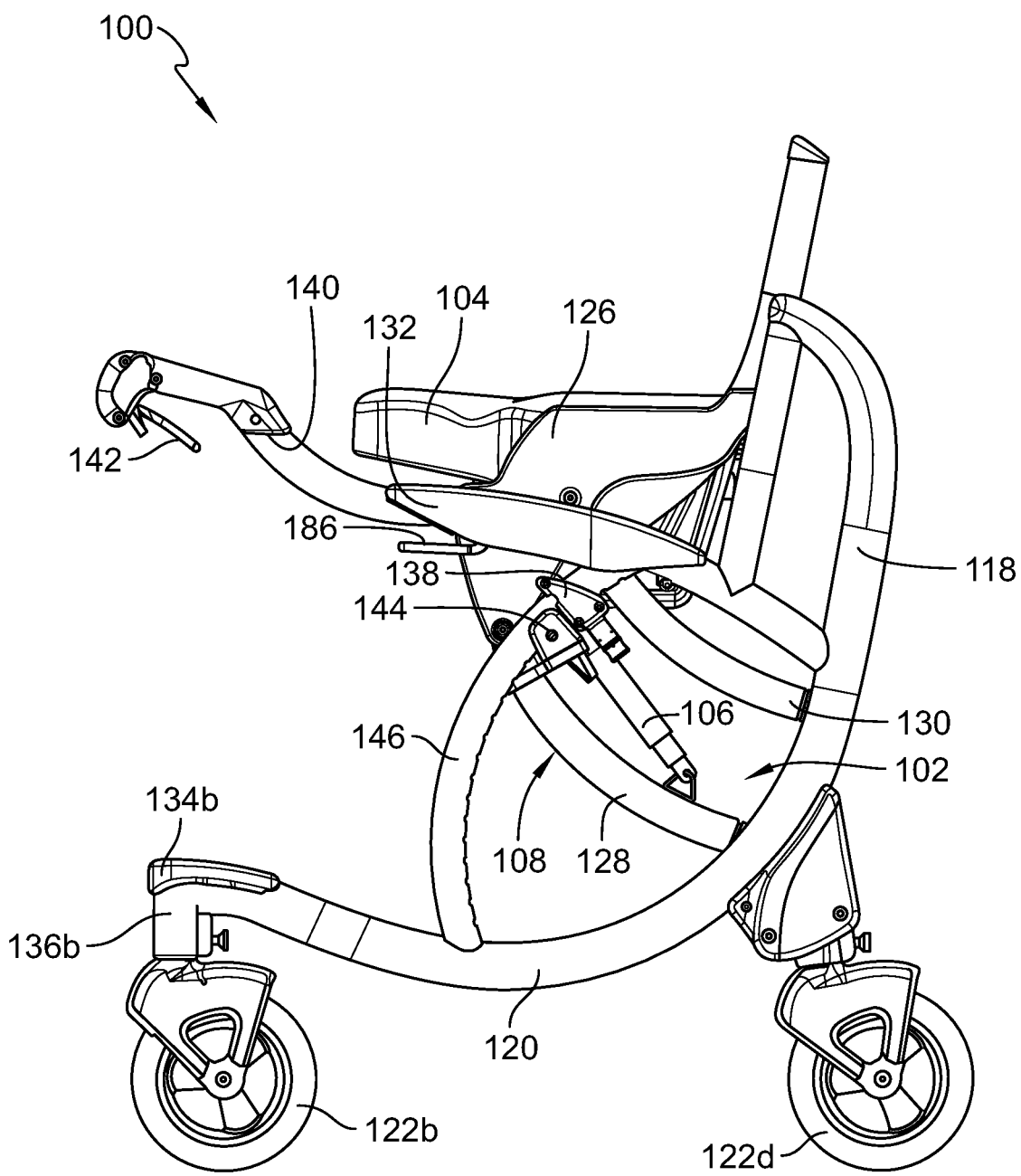
FIG. 2 depicts a side view of an elevating walker chair in a standing or walking mode with handle bars folded rearward.
Figure 3:
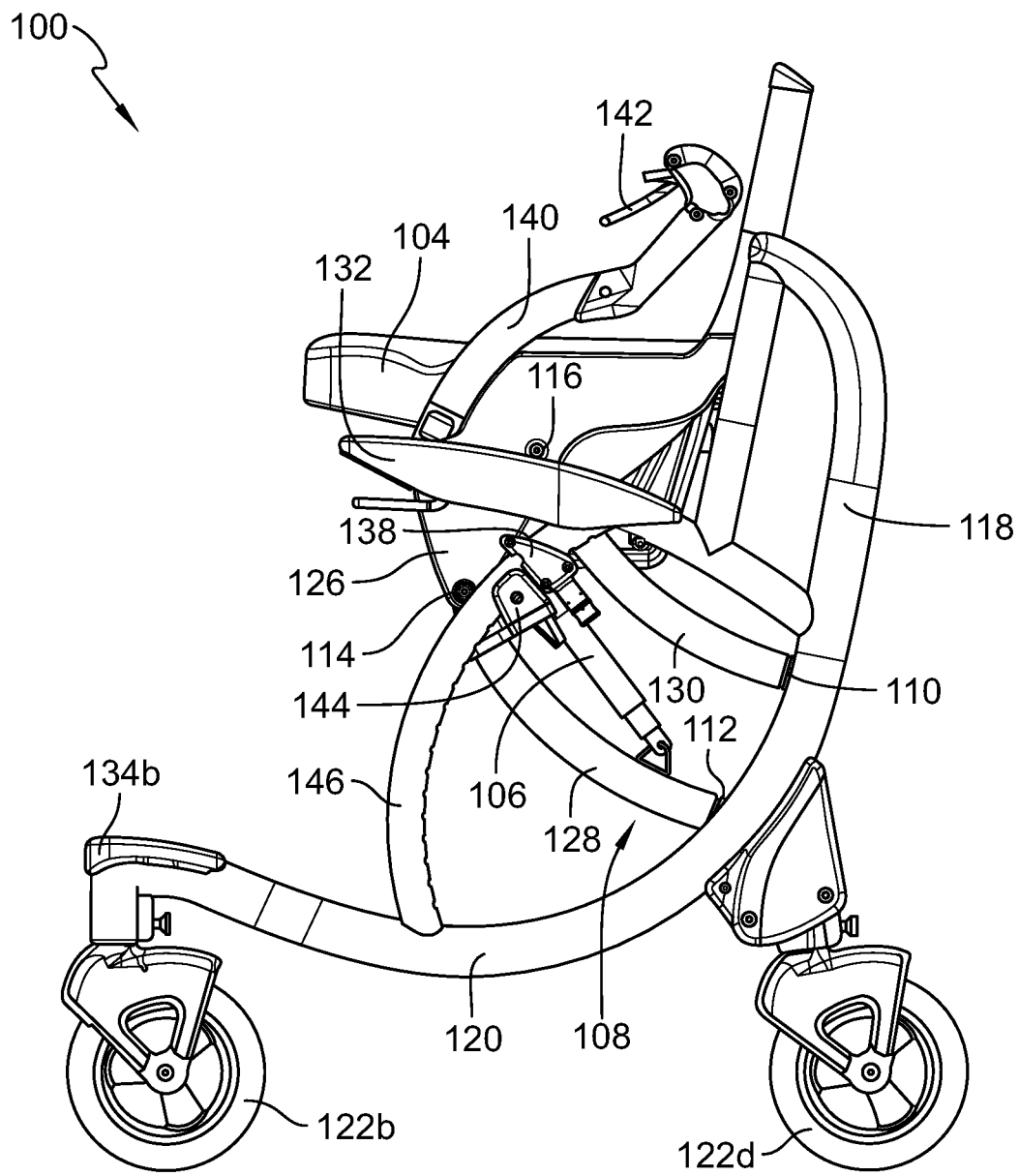
FIG. 3 depicts a side view of an elevating walker chair in a 'barstool' mode.
Figure 4:
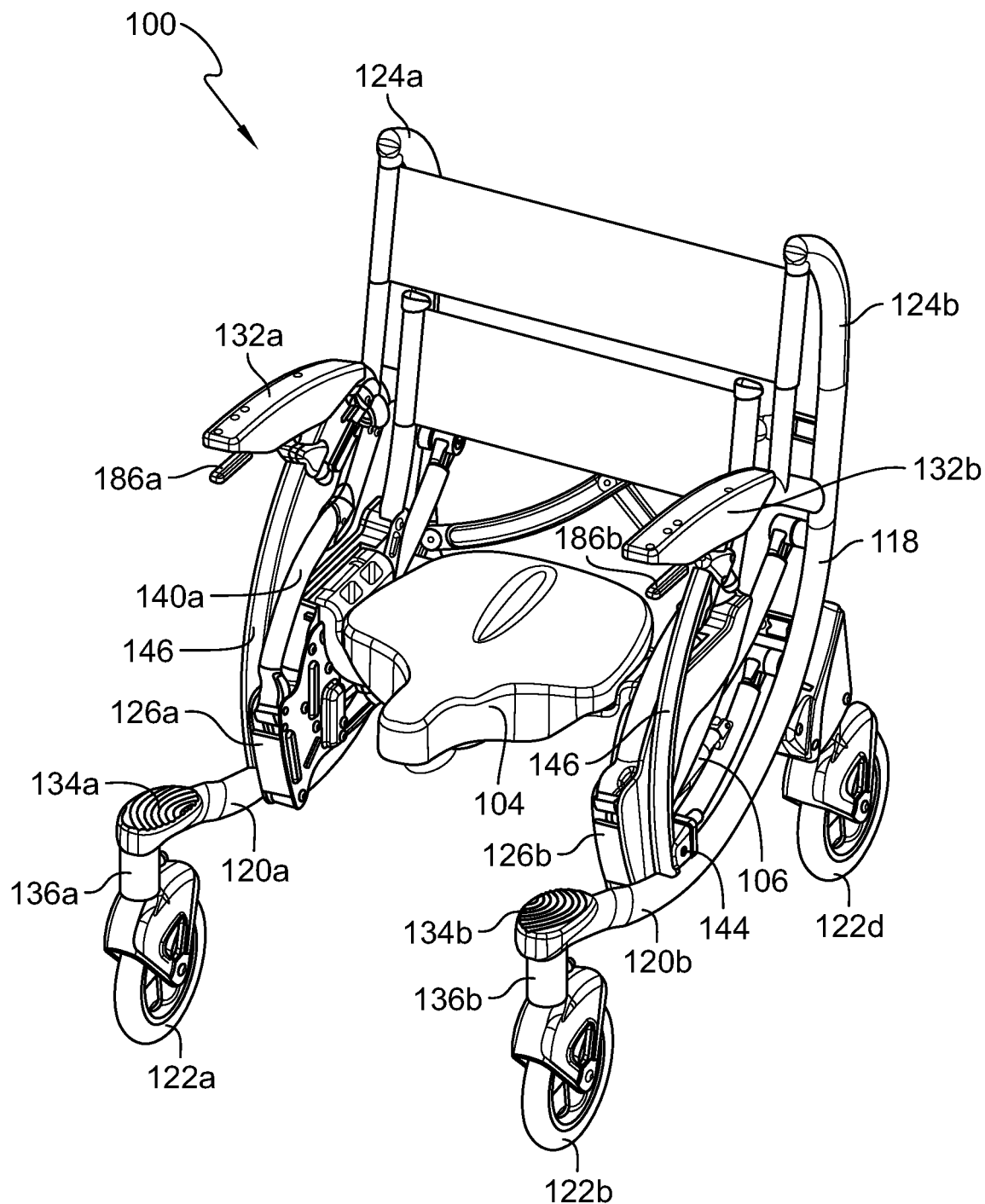
FIG. 4 is an isometric perspective view of an elevating walker chair in a sitting mode.
Figure 5:
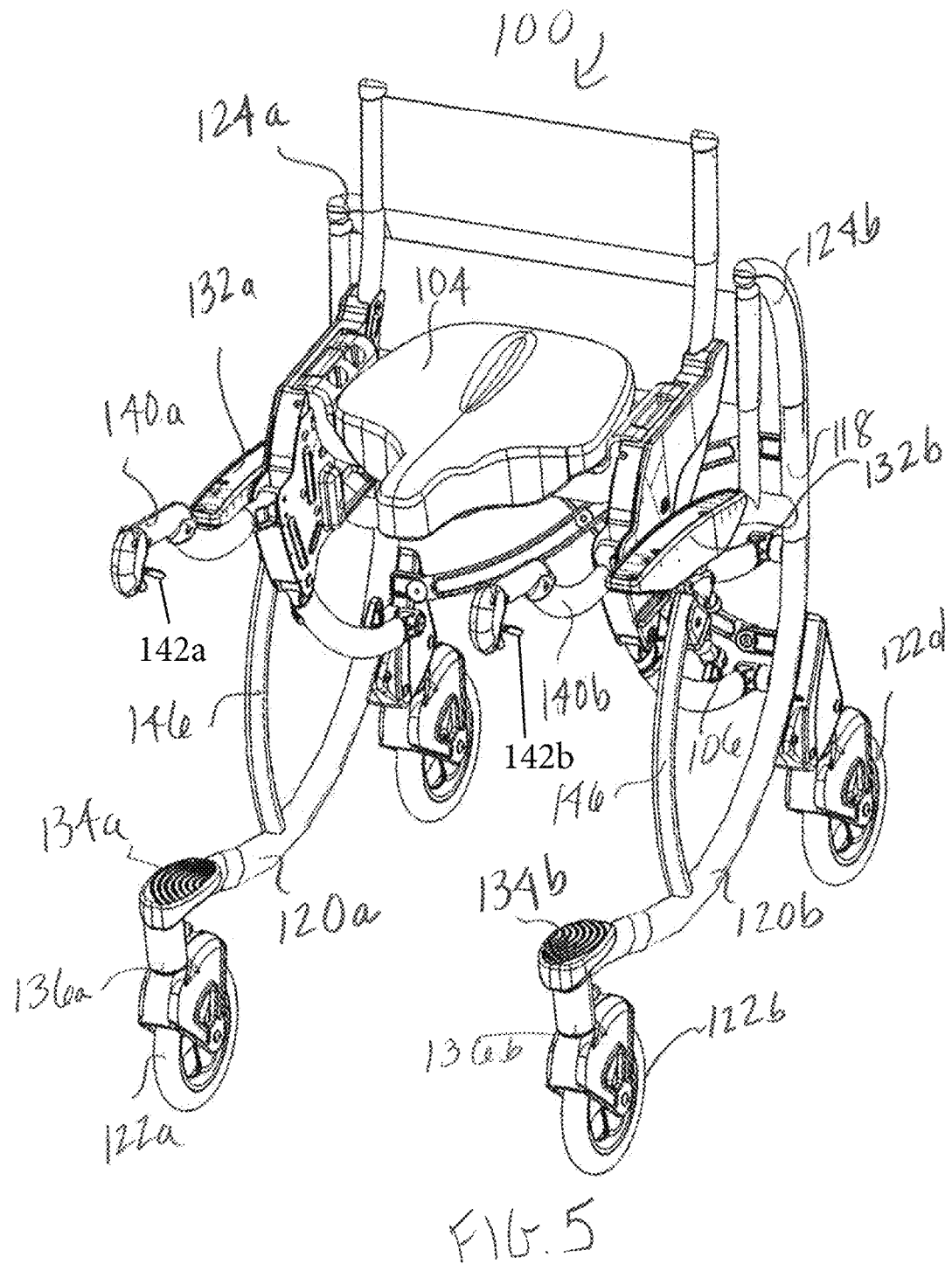
FIG. 5 depicts an isometric perspective view of an elevating walker chair in a standing or walking mode.
Figure 6:
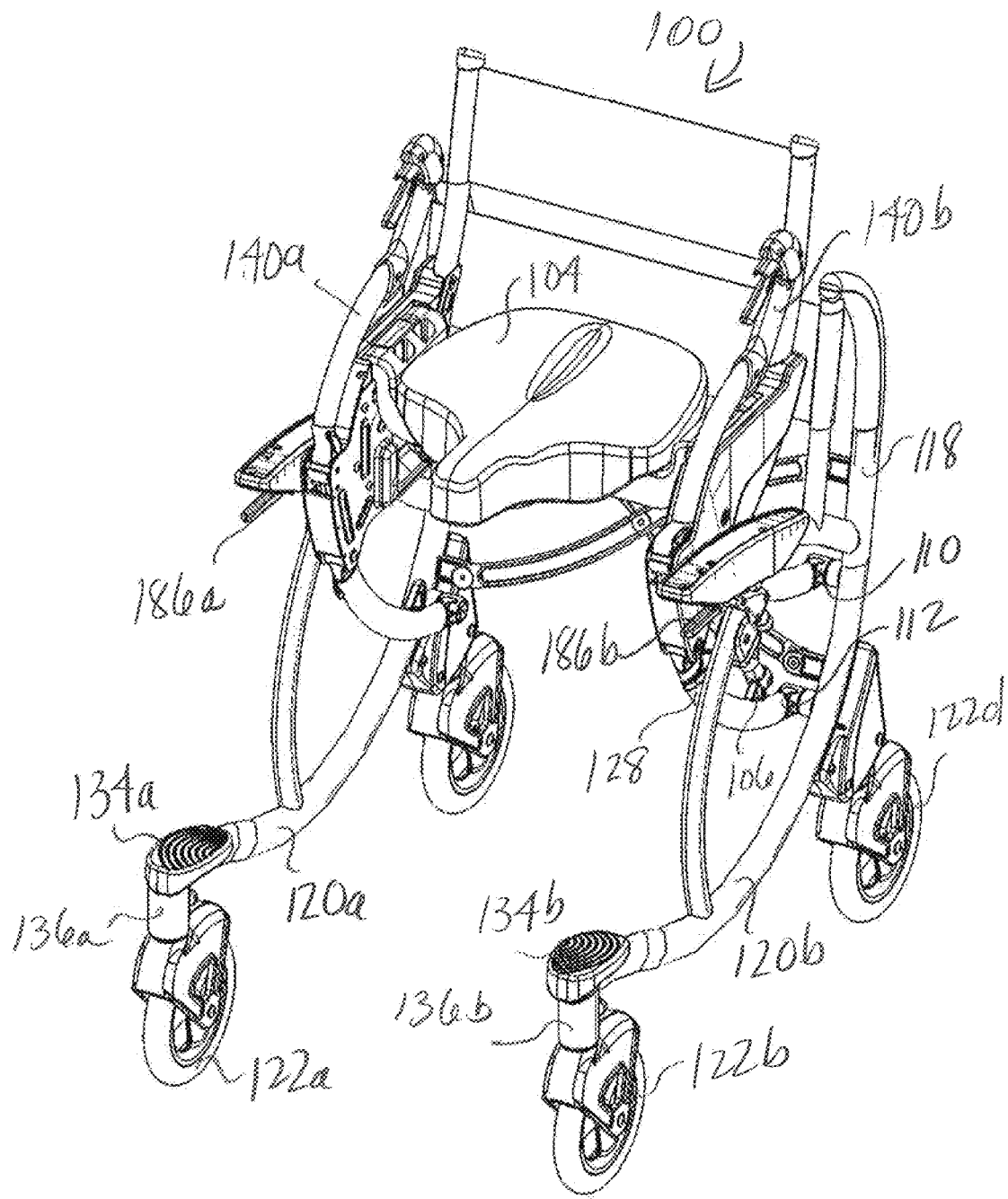
FIG. 6 depicts an isometric perspective view of an elevating walker chair in a 'barstool' mode with handle bars folded rearward.

FIGS. 1-6 depict an illustrative elevating walker chair 100, having a lifting mechanism 102 incorporated therein. FIGS. 1-3 show side views of elevating walker chair 100, and FIGS. 4-6 depict isometric views. Elevating walker chair 100 has a sitting mode in which seat 104 is in a lowered position, such as shown in FIGS. 1 and 4. Elevating walker chair 100 also has a standing or walking mode in which seat 104 is raised to allow an occupant to walk while being supported by the elevating walker chair, such as shown in FIGS. 2 and 5. In the standing or walking mode, handle bars 140a, 104b may be extended to allow a user to control elevating walker chair 100, for example, by activating brakes via brake handles 142a, 142b. Elevating walker chair 100 may have one or more brake handles 142.

FIGS. 3 and 6 depict elevating walker chair 100 in a barstool mode, which is a raised position in which handle bars 140a, 140b are folded rearward to allow a user to position elevating walker chair 100 close to a table, bar or counter, for example. Various seat heights may also be selected between the heights of seat 104 in the sitting mode and walking mode. Handle bars 140a, 140b may be folded rearward in the sitting mode or any raised seat position of elevating walker chair 100. This allows a user to position elevating walker chair closer to a table or desk or other apparatus.

Although seat 104 is depicted as a saddle, which may be advantageous for an elevating walker chair, seat 104 may have other configurations compatible with the use of elevating walker chair 100. Note the clearance in the front of elevating walker chair 100, as seen. for example in FIG. 4, which allows an occupant to interact with the environment using a normal walking gait without, or with little, obstruction of the occupant's legs.

FIGS. 1-3 depict lifting mechanism 102 having a spring 106 visible on one side. However, a lifting mechanism 102 with a spring 106 may also be incorporated into the opposing side of elevating walker chair 100. A lifting mechanism 102 may also be disposed centrally beneath seat 104. Other lifting mechanism structures can be incorporated into elevating lifting chair 100, either as a single unit or multiple units.

As can be seen in FIG. 3, for example, lifting mechanism 102 comprises a parallelogram structure 108 comprising parallelogram pivots 110, 112, 114, 116. Imaginary straight lines connecting parallelogram pivots 110. 112, 114, 116 form a parallelogram. Thus, the term "parallelogram," for example in the phrase "parallelogram structure" is used even though the actual structural links may not be linear. A portion of end block 126 forms a parallelogram link between parallelogram pivots 114, 116. A portion of a frame 118 forms a parallelogram link between pivots 110, 112. Parallelogram link 128 corresponds to the imaginary line between parallelogram pivots 112, 114. Parallelogram link 130 corresponds to the imaginary line between parallelogram pivots 110, 116.

Various components are attached to frame 118, either directly or indirectly, or integral therewith. As shown in FIG. 4, frame 118 may comprise lower frame components 120a, 120b to which wheels 122a-122d are attached. Frame 118 may include back components 124a, 124b that extend upward from lower frame components 120a, 120b, and which may be attached thereto, or integral therewith.

Armrests 132a, 132b are attached to frame 118. Optional footrests 134a, 134b are attached to frame 118 at footrest pivots 136a, 136b. Footrests 134a, 134b may be stationary with respect to frame 118 or free to rotate along with wheels 122a, 122b, and thus, used to steer elevating walker chair 100, as will be explained further below.

A steering mechanism may be included that incorporates one or both of footrests 134a, 134b, one or both of wheels 122a, 122b and one or both of footrest pivots 136a, 136b. Footrests 134a, 134b can be attached directly or indirectly to wheels 122a, 122b so that rotation of footrests 134a, 134b rotates wheels 122a, 122b. A user may move their foot or feet while engaged with footrests 134a, 134b to change the direction of footrests 134a, 134b, and thus, wheels 122a, 122b. Footrests 134a, 134b may have two or more standard positions, for example, folded in and pivoted inward to accommodate a user's feet while sitting. A footrest rotation mechanism to limit rotation of footrests 134a, 134b at pivot 136a, 136b may be employed, such as a rotational limit stop at the two or more positions. Other footrest rotation mechanisms that provide additional selection of positions may be included. See also FIGS. 32-34 and associated description below.

One or more of wheels 122a, 122b, 122c, 122d may be incorporated into elevating lifting chair 100 via conventional or dual-state casters, such as described in International Patent Application PCT/US2017/060163, filed Nov. 7, 2017, and incorporated herein by reference.

Figure 7:
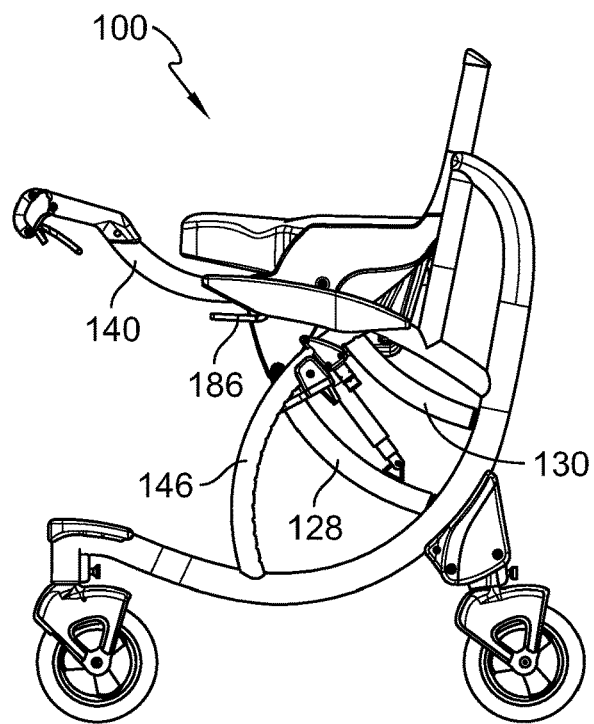
FIG. 7 depicts a side view of elevating walker chair with a maximum height limiter and a height adjustment mechanism, and an enlargement thereof.
Figure 7A:
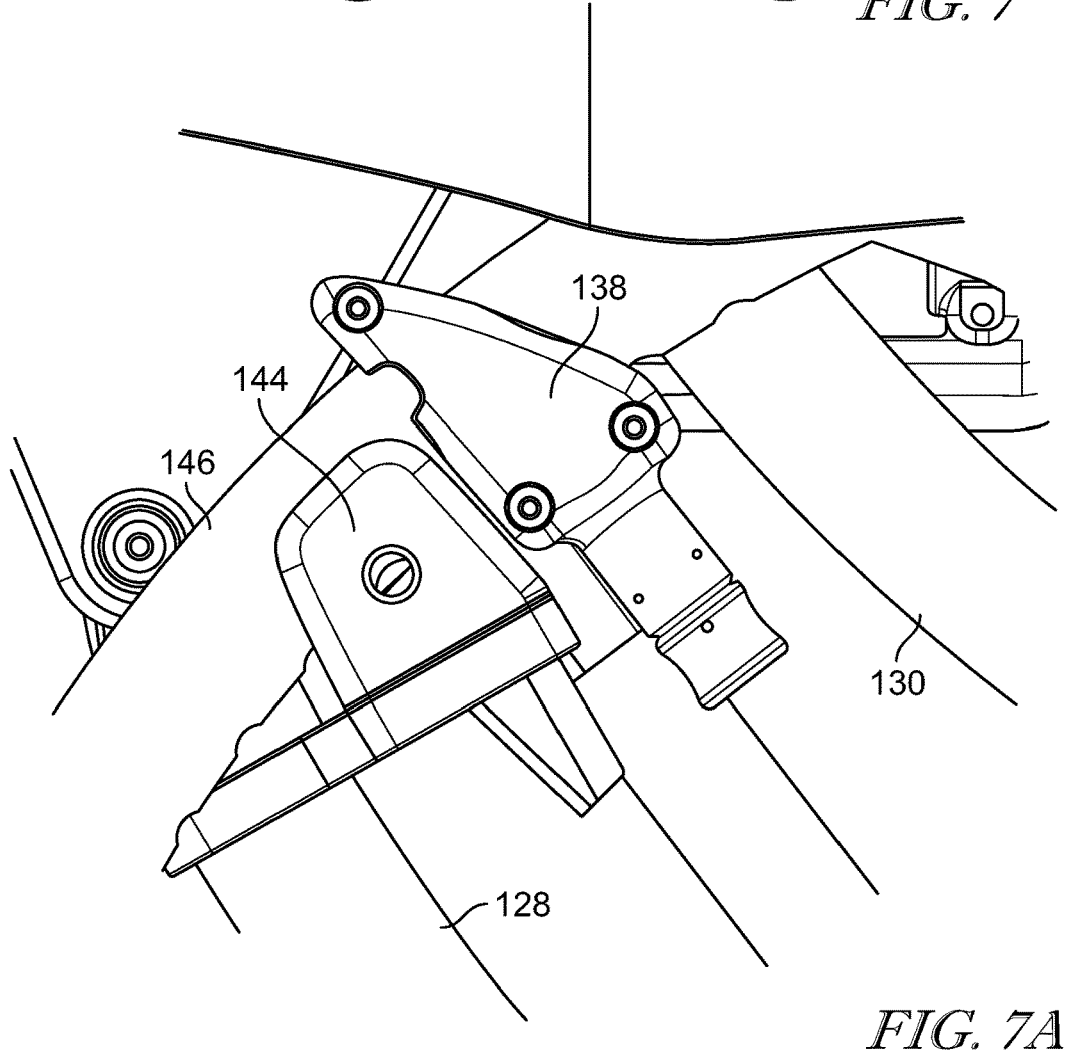

FIG. 7 and detail L of FIG. 7 depict an elevating walker chair 100 having a maximum height limiter 138, which may be set for example, to a user's standing or walking mode height. FIG. 7 also shows a height adjustment mechanism 144 for selecting various heights below the maximum height. An enlargement of a portion L of maximum height limiter 138 and height adjustment mechanism 144 is also shown. Seat height release lever arms 186a, 186b, when depressed while a user's weight is on seat 104, allow elevating walker chair 100 to be adjusted to a desired mode, such as sitting, standing/walking or barstool mode.

Figure 11:
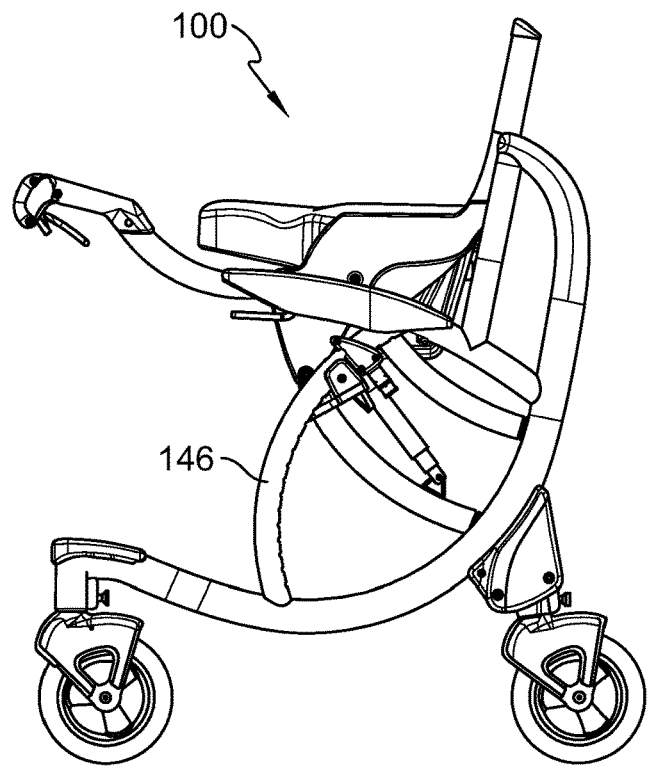
FIG. 11 depicts an oval tubular height adjustment strut and a lateral cross-sectional view.
Figure 11A:
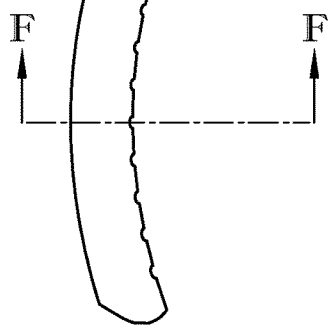
Figure 11B:
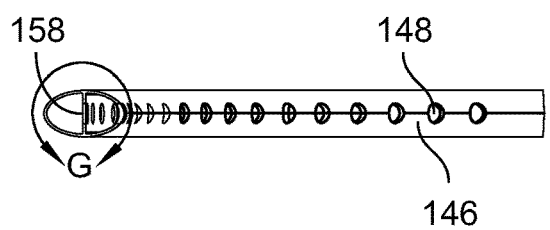
Figure 11C:
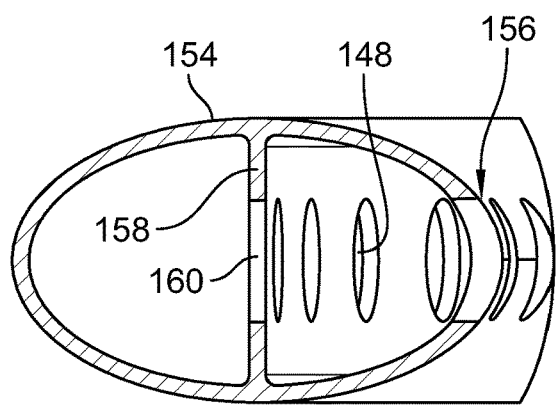
Figure 12:
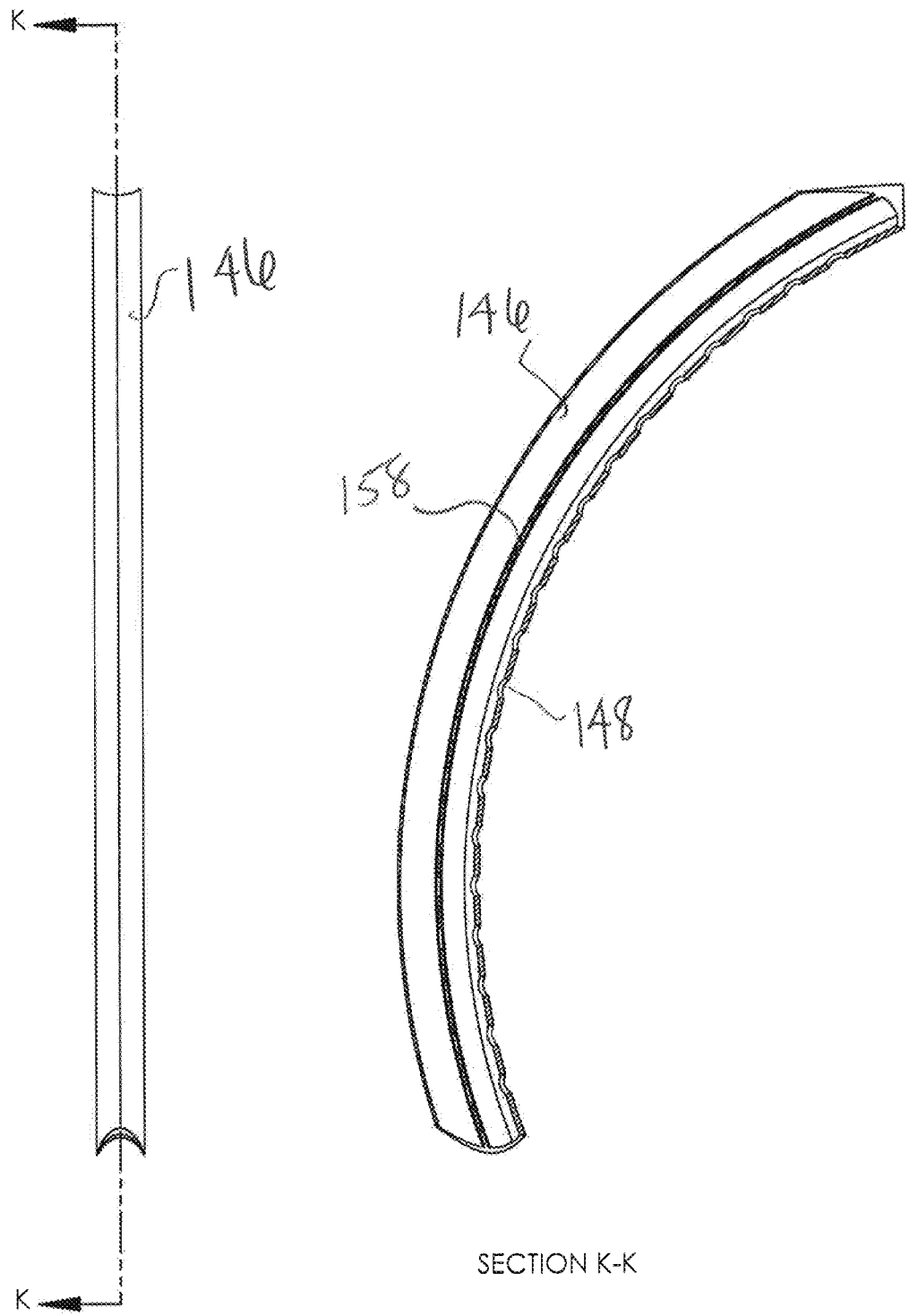
FIG. 12 is a longitudinal cross-sectional view of the oval tubular height adjustment strut of FIG. 11.

In the illustrative embodiment depicted in FIG. 7, maximum height limiter 138 includes a bracing and height adjusting strut 146 having a series of holes 148 in its wall 154 (see also FIGS. 11 and 12). Height adjustment bar 146 functions as part of maximum height limiter 138 and height adjustment mechanism 144, which will be described in more detail below.

Figure 9:
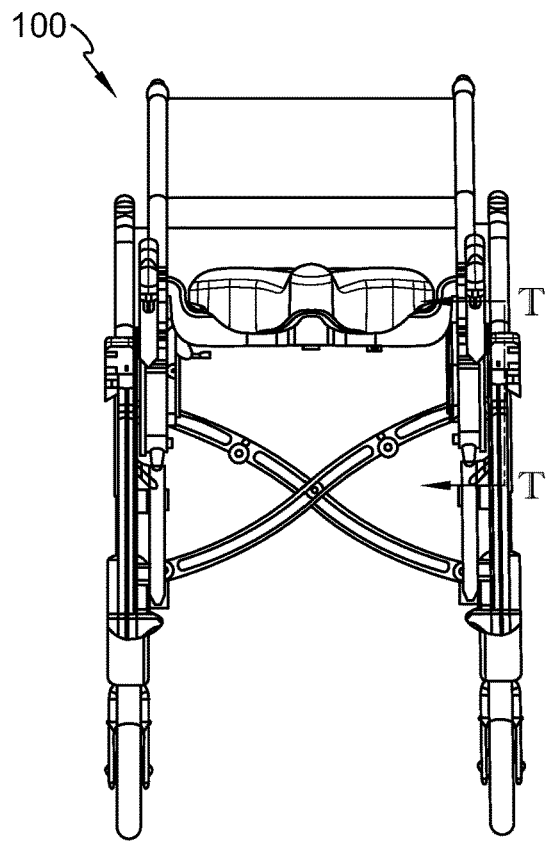
FIG. 9 depicts a front view of elevating walker chair with a maximum height limiter and a height adjustment mechanism, and a further cross-sectional enlargement thereof, wherein height adjustment pins are engaged with a height adjustment strut.
Figure 9A:
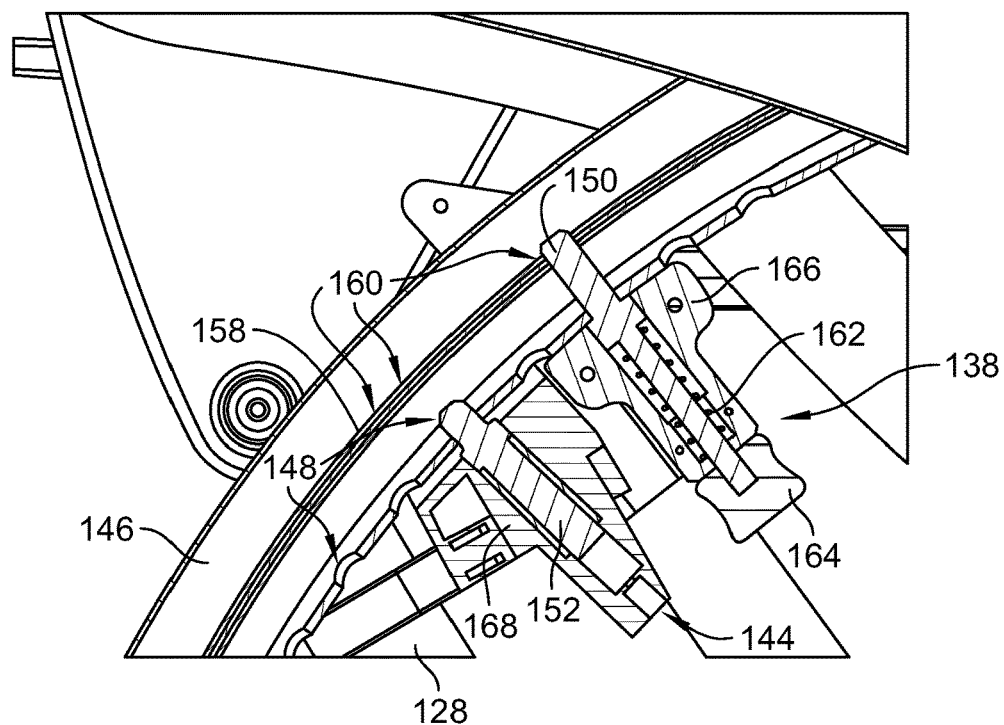
Figure 10:
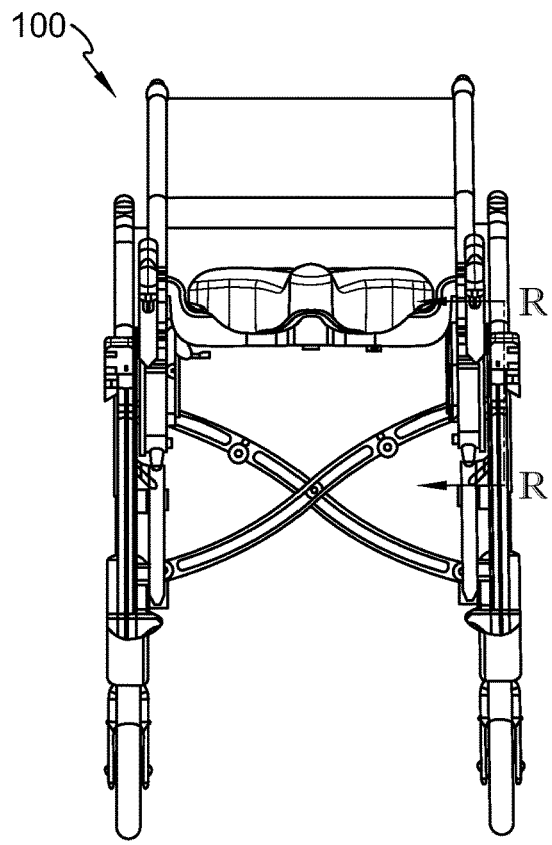
FIG. 10 depicts a front view of elevating walker chair with a maximum height limiter and a height adjustment mechanism, and a cross-sectional enlargement thereof, wherein the height limiter pin is disengaged with a height adjustment strut.
Figure 10A:
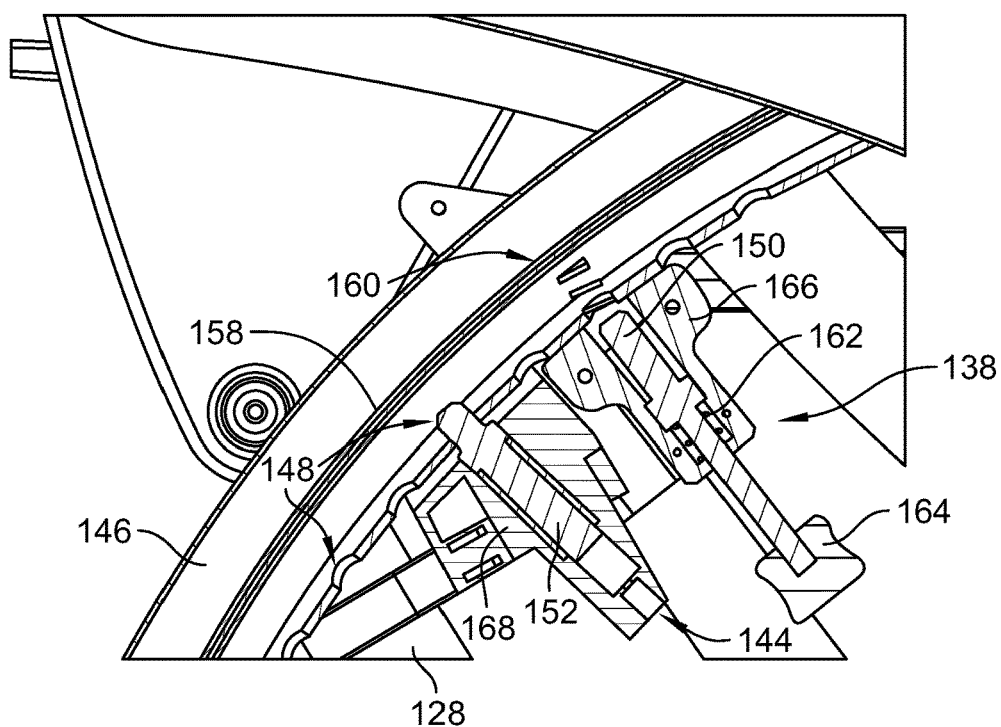

FIGS. 9-10 depict cross-sections through maximum height limiter 138 and height adjustment mechanism 144. FIG. 9 shows a cross-section detail through line T-T, both depicting a maximum height limiter pin 150 and height adjustment pin 152 engaged in holes 148, 160 in height adjusting strut 146. FIG. 10 shows maximum height limiter pin 150 disengaged hole 160 in height adjusting strut 146.

Details of bracing and height adjusting strut 146 are shown in FIGS. 11 and 12. FIG. 11 shows height adjusting strut 146 with a lateral cross-section F-F and an enlargement G of the cross-sectional view. FIG. 12 depicts height adjusting strut 146 and a longitudinal cross-section through K-K.

In the illustrative embodiment shown in FIG. 11, height adjusting strut 146 is a tube having an oval cross-section. Adjustment strut 146 is shown as a curved member, but in alternative embodiments may be linear, provided it can serve the function as described herein. In an illustrative embodiment, height adjustment pin 152 is associated with a parallelogram link and travels arctuately. Other cross-sectional shapes may be used, provided that the height adjustment mechanism 144 and maximum height limiter 138 are configured to coordinate with the shape to carry out their respective functions. adjusting and limiting height, respectively. The strut wall 154 of height adjusting strut 146 may be thickened in strut wall area 156 to inhibit wear and tear from height adjustment pin 152 and maximum height limiter pin 150. Height adjusting strut 146 may have a cross-web 158. As noted previously, height adjusting strut 146 has holes 148 in its wall 154. Height adjusting strut 146 also has holes 160 in cross-web 158. Cross-web holes 160 are aligned with strut wall holes 148.

Advantageously, adjusting strut 146 can be a support strut when employed in the elevating walker chair configurations disclosed herein. This allows a lighter weight elevating walker chair because use of additional, heavier or more extensive lifting mechanisms may be avoided.

Figure 8:
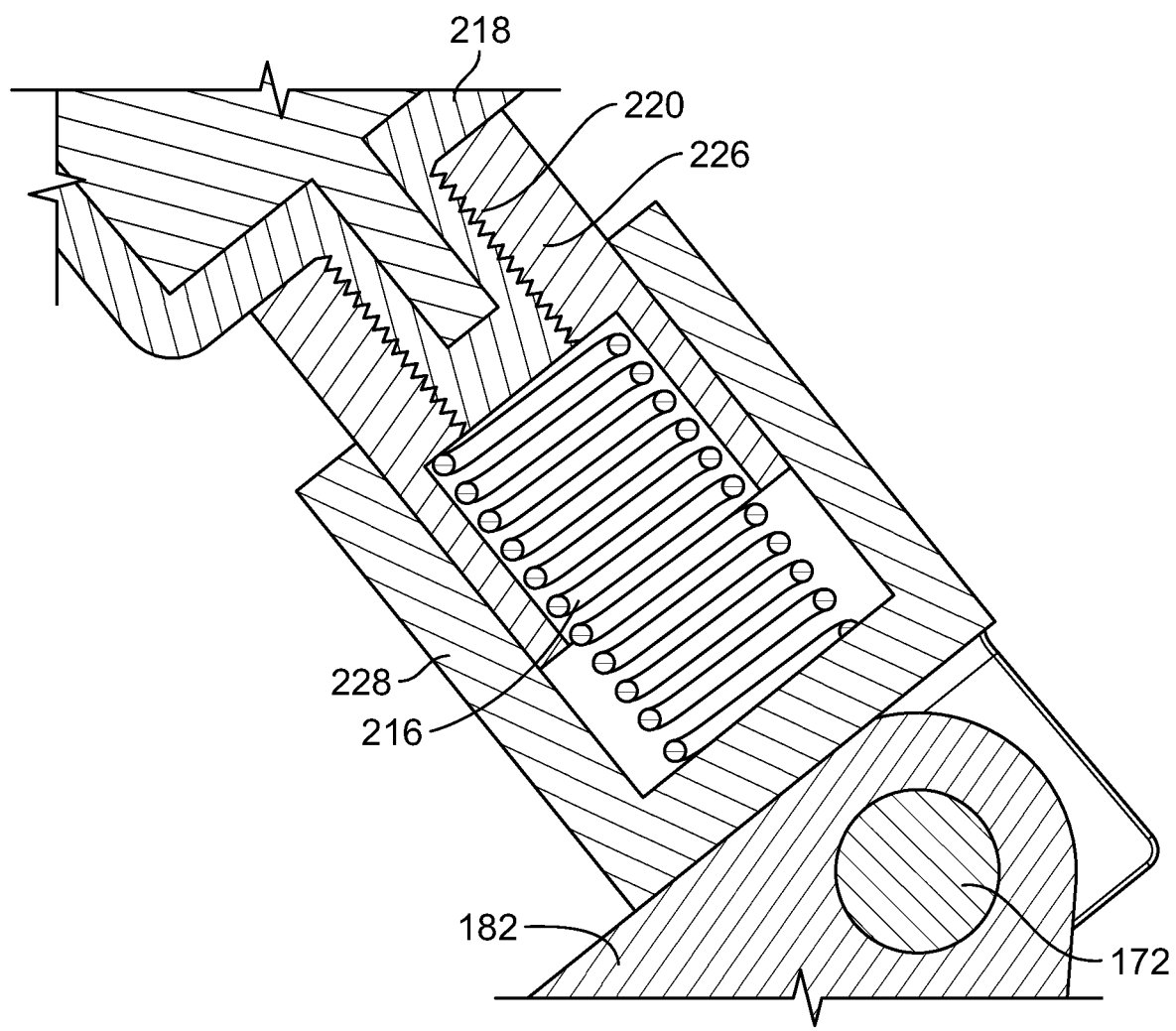
FIG. 8 depict a spring arrangement that facilitates adjustment of lifting strength by keeping a spring pin engaged when the elevating walker chair is fully lifted.

As shown in FIGS. 8 and 9, height adjustment pin 152 extends into a hole 148 in height adjustment strut wall 154, but does not extend through a cross-web hole 160. In an illustrative embodiment, height adjustment pin 152 engages to about the thickness of height adjustment strut wall 154. Maximum height limiter pin 150, however, extends through height adjustment strut wall holes 148 and through cross-web holes 160. This may help to stabilize maximum height limiter pin 150.

Maximum height limiter 138 has a compression spring 162 disposed around maximum height limiter pin 150 as shown in the cross-sectional drawings of FIGS. 9 and 10. A grip 164 may be attached to maximum height limiter pin 150 to facilitate a user withdrawing maximum height limiter pin 150 from cross-web hole 160 and height adjustment strut wall hole 148, and sliding maximum height limiter 138 along height adjusting strut to change the maximum height limit. Once maximum height limiter pin 150 is aligned with a height adjustment strut hole 148 (and thus automatically also aligned with a cross-web hole 160), compression spring 162 will bias maximum height limiter pin 150 to extend and remain through holes 148, 160. A maximum height limiter housing 166 surrounds compression spring 162 and maximum height limiter pin 150. Maximum height limiter housing 166 is slidably engaged with height adjusting strut. Grip 164 is disposed outside of maximum height limiter housing 166. Maximum height limiter pin 150 extends through an opening at a first end of maximum height limiter housing 166, and through an opposing opening in maximum height limiter housing 166 when compression spring 162 is extended.

Height adjustment mechanism 144 height adjustment mechanism housing 168. Height adjustment pin 152, when in its extended position, extends through an opening in height adjustment mechanism housing 168, and through a height adjustment strut wall hole 148.

Figure 38:
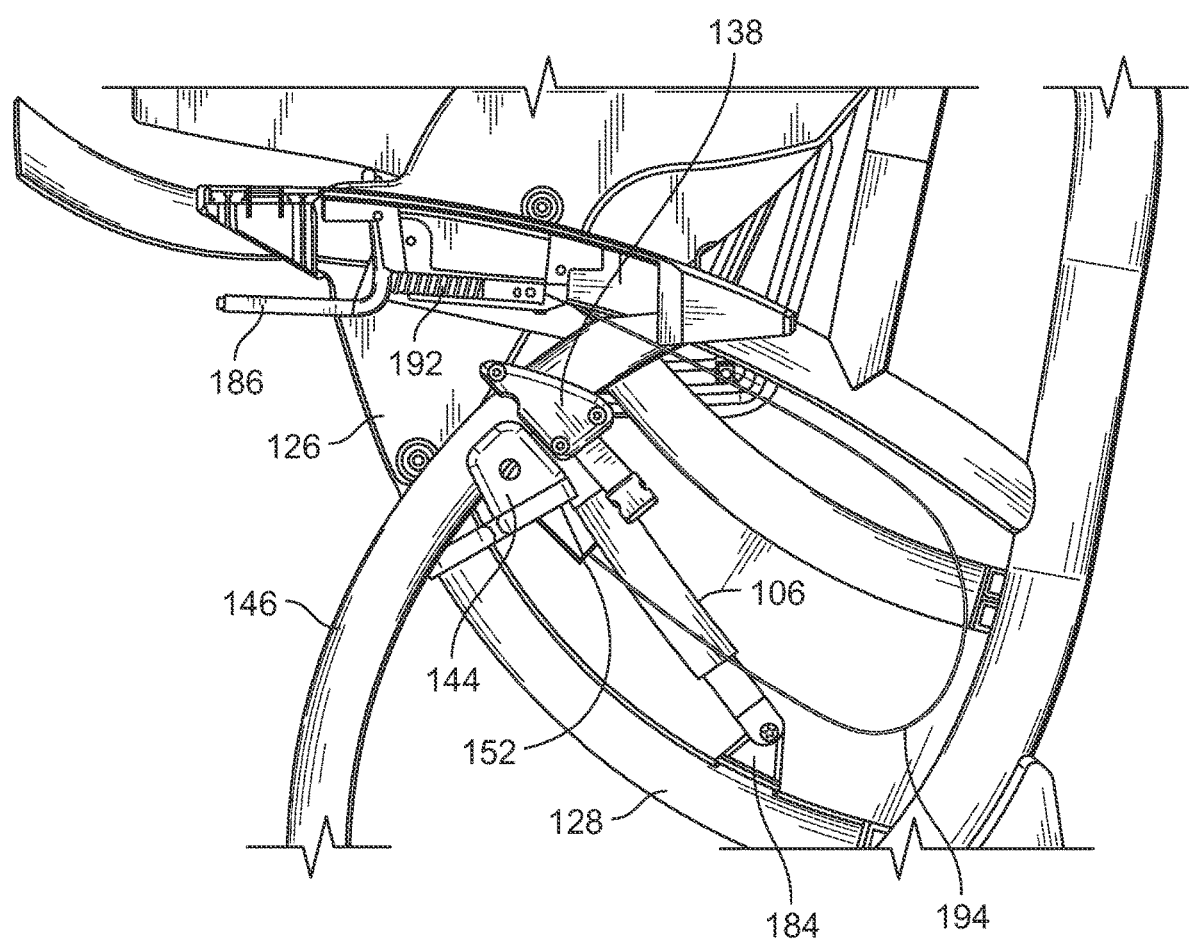
FIG. 38 shows additional components of a seat height lock safety mechanism.

FIGS. 37 and 38 depict cut-aways of a seat height lock safety mechanism. The cut-away of FIG. 37 is identified as detail C, which is an enlargement of a portion of elevating walker chair 100 seen in a view taken along B-B. Extension spring 192 is connected to seat height release lever 186 so that compression of seat height adjustment lever 186 causes extension spring 192 to expand under certain conditions, which will be explained further below. As seen in FIG. 38, a cable 194 extends from height adjustment pin 152 and terminates at seat height adjustment lever 186, which is also connected to extension spring 192. When seat height adjustment lever 186 is compressed, height adjustment pin 152 may be removed from height adjustment strut wall holes 148, unless the friction between height adjustment pin 152 and height adjustment strut wall holes 148 is too great. The height lock safety mechanism is configured so that the friction between height adjustment pin 152 and height adjustment strut wall holes 148 keeps height adjustment pin 152 in place when there is no weight on seat 104, i.e. when the seat is unoccupied. When a user is seated, and elevating walker chair 100 is adjusted for the user's weight, there is no, or nearly no, upward or downward bias of the seat, i.e. the seat is equipoised or near equipoised. This balance frees height adjustment pin 152 to be retracted because friction is minimized. Equipoising and biasing of the seat may be achieved, for example, by spring 106 and parallelogram structure 108, as illustrated in FIG. 3, for example. Once a user departs from elevating walker chair 100, the seat is biased, thereby creating a frictional force between height adjustment pin 152 and the height adjustment strut wall hole 148 in which it is inserted. Accordingly, when elevating walker chair 100 is unoccupied, height adjustment pin 152 remains in place.

Turning back to FIGS. 9 and 10, height adjustment mechanism housing 168 is fixedly attached to parallelogram link 128. Therefore, as height adjustment mechanism housing 168 is moved along height adjusting strut, the angles in parallelogram structure 108 change, thereby raising or lowering seat 104.

When maximum height limiter 138 is engaged with height adjusting strut, the excursion of height adjustment mechanism housing 168 along height adjusting strut is limited.

Maximum height limiter housing 166 is shown as a full sleeve around height adjusting strut. Height adjustment mechanism housing 168 is shown as only partially encircling height adjusting strut. Either housing may fully or partially surround height adjusting strut, provided they are slidable with respect to height adjusting strut, and their respective pins can properly engage cross-web holes 160 and height adjustment strut wall holes 148, and not interfere with other components of elevating walker chair 100. Various mechanisms may be included to facilitate the housings sliding along height adjusting strut, for example, rollers, ball bearings and low-friction material, or combinations of such mechanisms.

It is noted that the "height limit" and "height adjustment" described with respect to maximum height limiter 138 and height adjustment mechanism 144 are different than the lifting-force adjustment provided by lifting mechanism 102, which will be described in more detail below. Maximum height limiter 138 provides a maximum height limit that defines the extent of the excursion generated by the lifting mechanism from a sitting mode to a standing mode. Height adjustment mechanism 144 allows a user to select a seat height between the sitting mode to a standing mode. Lifting mechanism 102 facilitates users of various body weights to readily change the momentary height of seat 104. Other configurations of height limiters and height adjustment mechanisms may be used with elevating walker chair 100.

Figure 13:
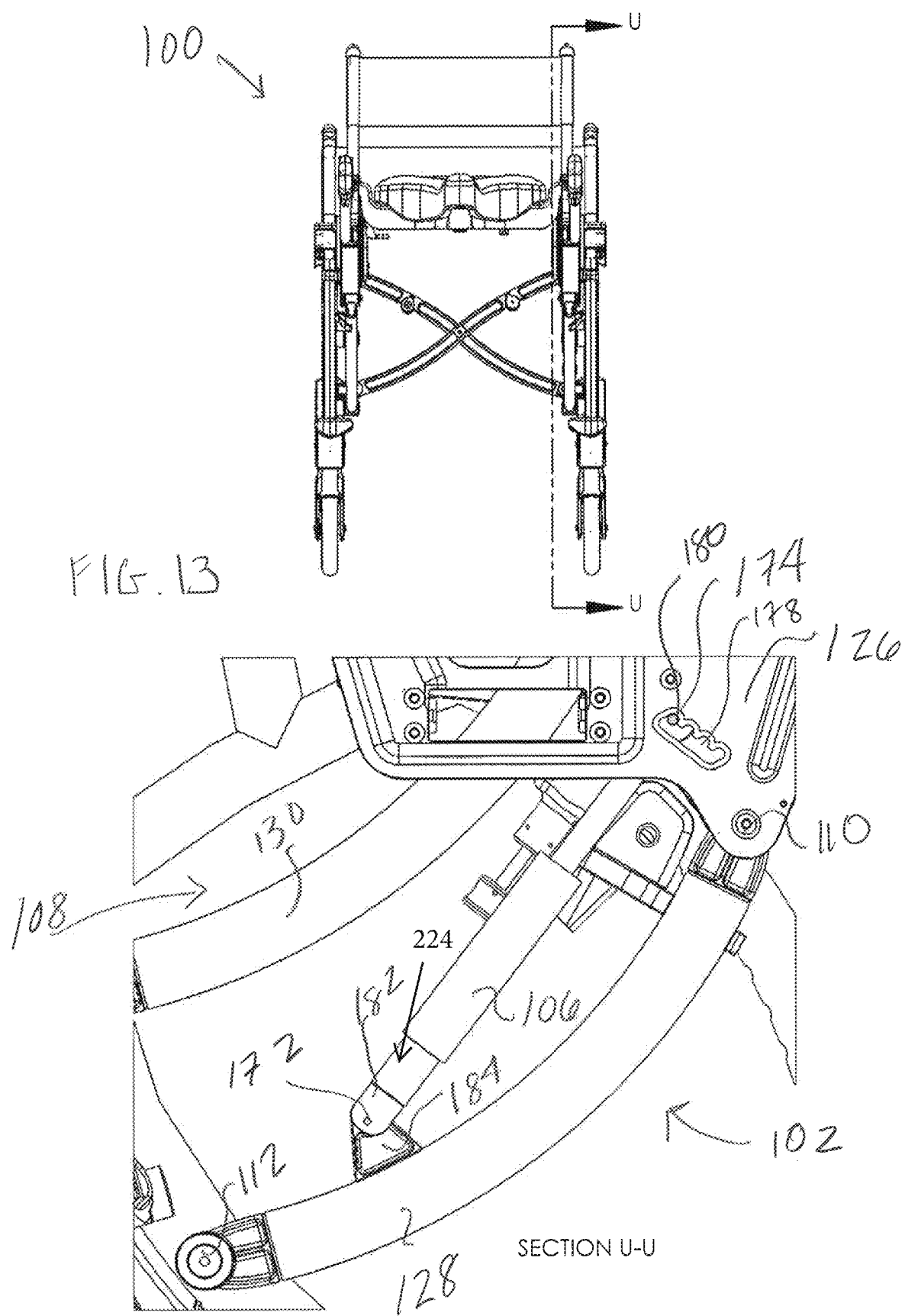
FIG. 13 depicts a front view of an elevating walker chair and a close-up view of components of a lifting mechanism.
Figure 14:
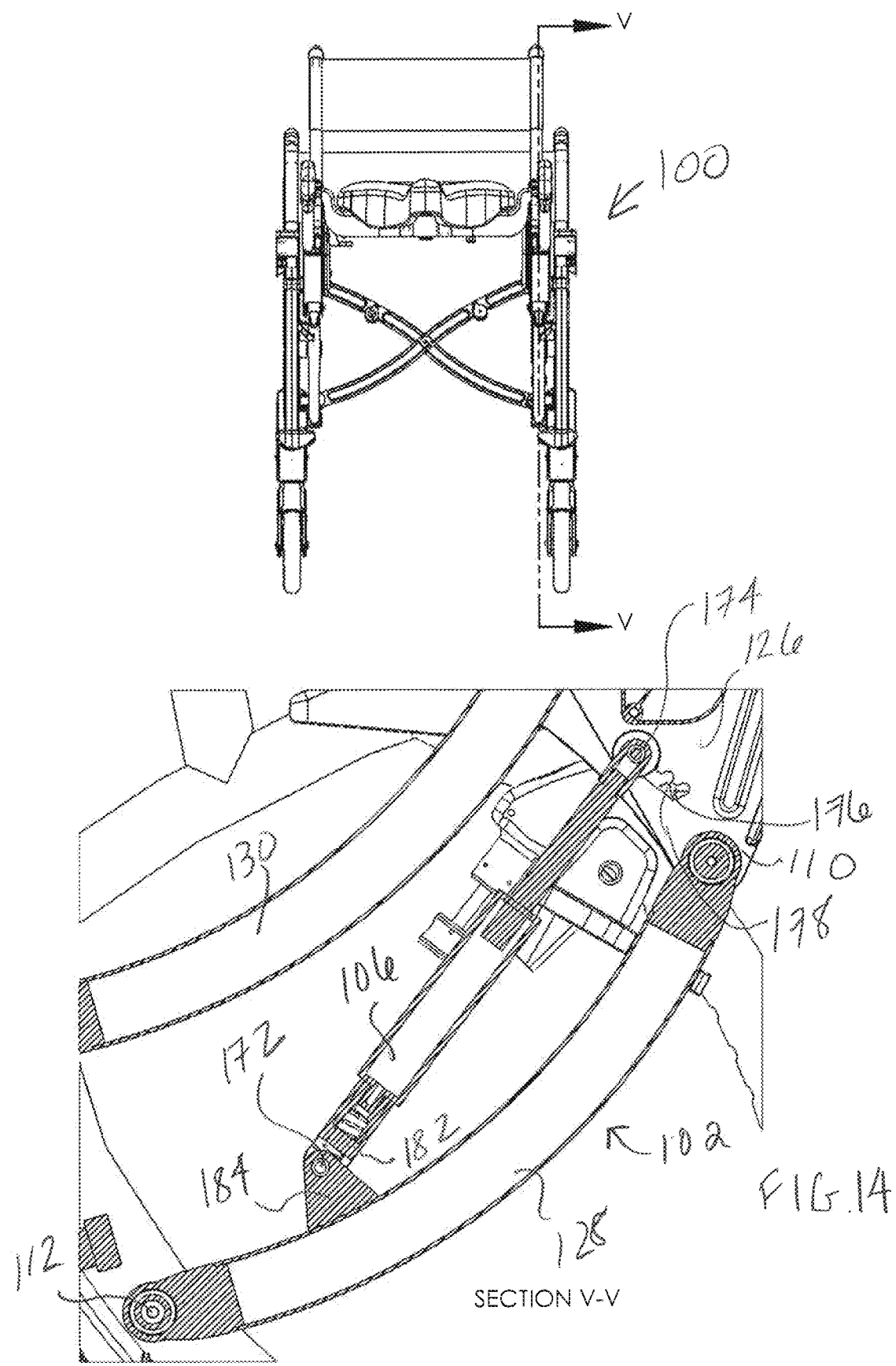
FIG. 14 depicts a front view of an elevating walker chair and a cross-sectional view of components of a lifting mechanism.

FIG. 13 depicts a front view of elevating walker chair 100 and a cross-sectional view through U-U, which shows components of lifting mechanism 102. FIG. 14 depicts a front view of elevating walker chair 100 and a cross-section view through V-V, which shows a cutaway cross-section of components of lifting mechanism 102. Lifting mechanism 102 includes parallelogram structure 108 (partially shown) and spring 106, such as a gas spring, for example. Spring 106 is attached at a first spring end to parallelogram link 128, and at a second spring end to end block 126. Spring 106 is rotatably attached to parallelogram link 128 at pivot 172. In this illustrative embodiment, spring 106 has a clevis 182 at its first end, which engages with a tab 184 that is fixedly attached to parallelogram link 128. The second end of spring 106 will be referred to as spring termination point 174. Spring termination point 174 serves as a pivot.

A lifting power mechanism may be employed. For example, spring 106 may be adjustably attached to end block 126 at spring termination point 174. End block has a slot 176, which in this illustrative embodiment has notches 178 appearing as a scalloped interior slot edge. Spring termination point 174 has a spring pin 180 that engages with slot 176 and remains in one of notches 178. Notches 178 form an arc with radii extending from spring pivot 172. The radius of slot 176 may match the pivoting radius of the second end of spring 106 when spring 106 is fully extended. The lifting force of lifting mechanism 102 will vary depending on with which notch spring pin 180 is engaged. An appropriate lifting force, and hence notch position, should be selected based on the weight of the occupant of elevating walker chair 100, as will be described in more detail below. Spring pin 180 will remain engaged in a notch 178 until height adjustment pin 152 and maximum height limiter pin 150 are disengaged from height adjustment strut wall holes 148 and moved beyond maximum height so that spring 106 is fully extended. Spring 106 can then be manually disengaged. Once spring pin 180 is withdrawn from notch 178 it may be relocated in a different notch 178 to adjust the lifting strength of lifting mechanism 102. See below for further explanation of the lift adjustment function.

To facilitate withdrawal of spring pin 180 from notch 178, an auxiliary compression spring 216 may be employed. FIG. 8 depicts an auxiliary spring mechanism that facilitates maintaining spring pin 180 in notches 178 of slot 176 when the elevating walker chair is fully lifted. The auxiliary compression spring mechanism may be housed in an end area 224, such as shown in FIG. 13. A portion of spring 106 is shown that includes a spring body 218 with a threaded mount portion 220. An extension cylinder 226 extends from spring body 218. Extension cylinder 226 is slidably engaged with a receiving cup 228, which is generally spring end area 224. Auxiliary spring 216 is co-axial with spring 106. In essence, auxiliary spring 216 extends the travel of spring 106, or takes over when spring 106 is fully extended, by expanding when the seat of the elevating walker chair reaches a maximum height. This expansion is configured to provide enough force to keep spring pin 180 in slot 176 but allowing it to be adjusted among the various notches 178.

Adjusting the location of spring termination point 174 shortens or lengthens a side of a lifting triangle that forms a part of lifting mechanism 102. This lifting triangle side is the distance from spring termination point 174 to parallelogram pivot 114 (see FIG. 3 for location of pivot 114). The other two sides of the lifting triangle are the length of spring 106 from spring pivot 172 to spring termination point 174, and the distance from spring pivot 172 to parallelogram pivot 114. The distance from spring termination point 174 to parallelogram pivot 114 may be considered a "lever arm." The effective lifting force of lifting mechanism 102 increases as the length of the lever arm increases.

In this illustrative embodiment, elevating walker chair 100 should be in its highest position to make a lifting strength adjustment. In the lowest position, spring 106 is compressed and positioned so it cannot be readily re-aligned with notches 178. Spring 106 is extended when elevating walker chair 100 is in its highest position and aligns with notches 178. Therefore, 180 can be more readily re-positioned in a selected notch 178.

Figure 16:
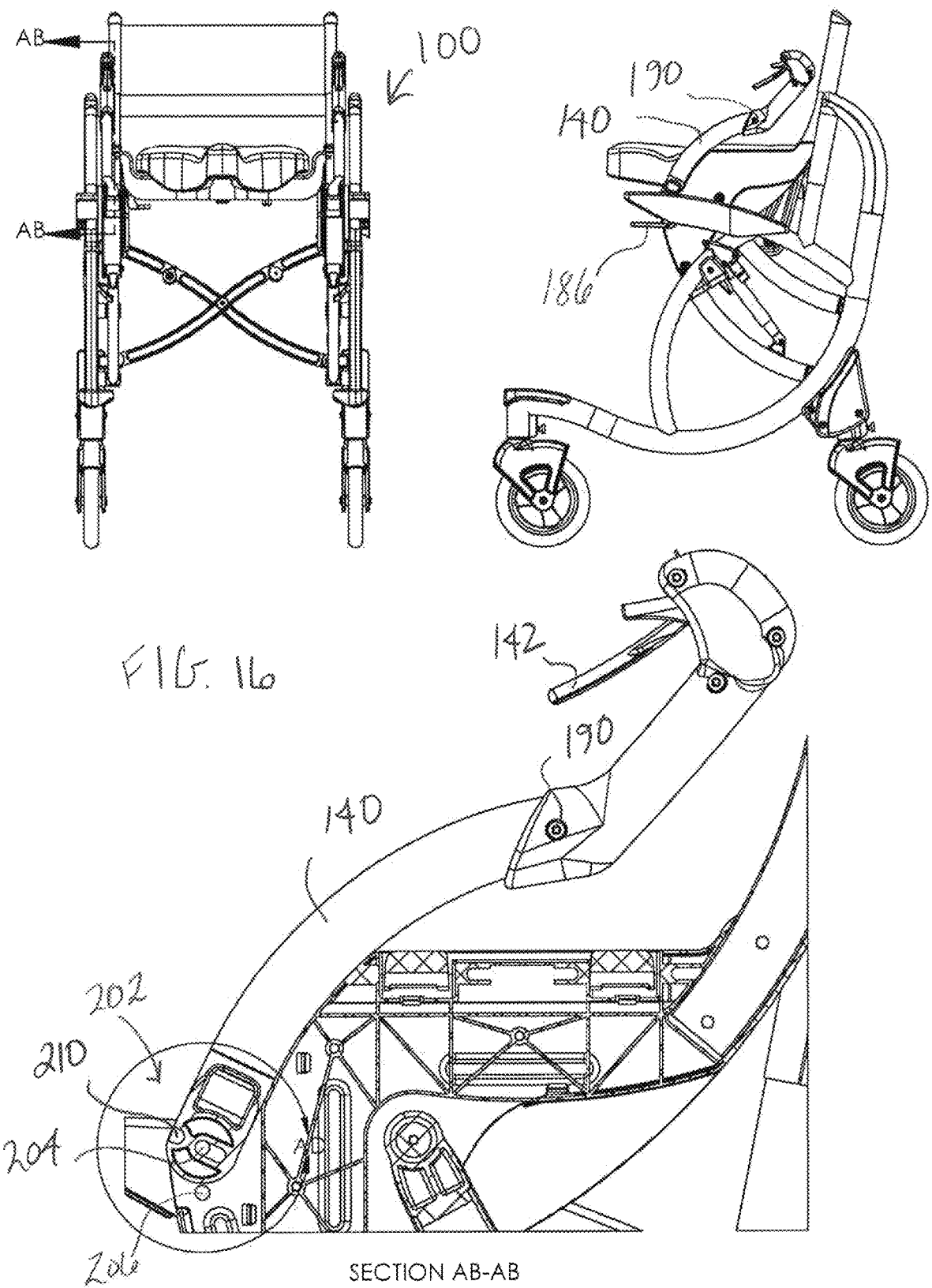
FIG. 16 depicts front and side views of an elevating walker chair having handle bars folded rearward, and a close up, cross-sectional view of a handle bar pivot.

As shown in FIGS. 15 and 16, elevating walker chair 100 has handle bars 140a, 140b (see also FIGS. 5 and 6). Handle bars 140a, 140b may comprise one or more sections. For example, as shown in FIG. 15, handle bars 140a, 140b have two components joined at fasteners 190a, 190b. Handle bars 140a, 140b are pivotably attached to end blocks 126a, 126b by handle bar pivots 202a, 202b. Handle bars 140a, 140b may accommodate a user in a comfortable and supportive manner when using elevating walker chair in a raised position to stand or walk. In an illustrative embodiment handle bars 140a, 140b are optionally configured to extend upon raising elevating walker chair 100. Alternatively, or additionally, handle bars 140a, 140b may be configured to be manually deployed.

Figure 17:
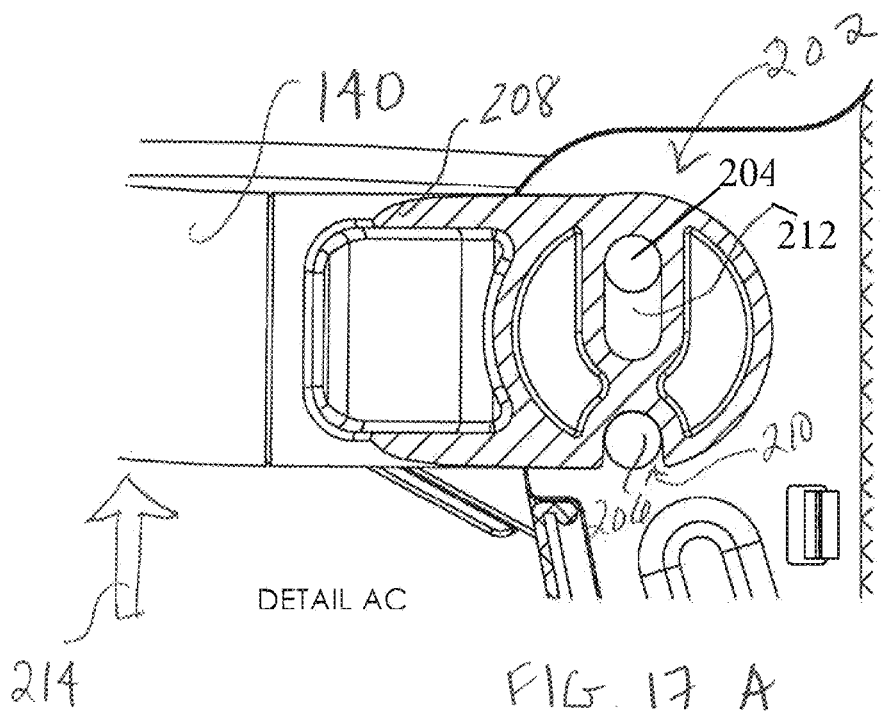
FIGS. 17A, 17B depict cross-sectional views of a handle bar pivot in extended and folded modes, respectively.
Figure 17:
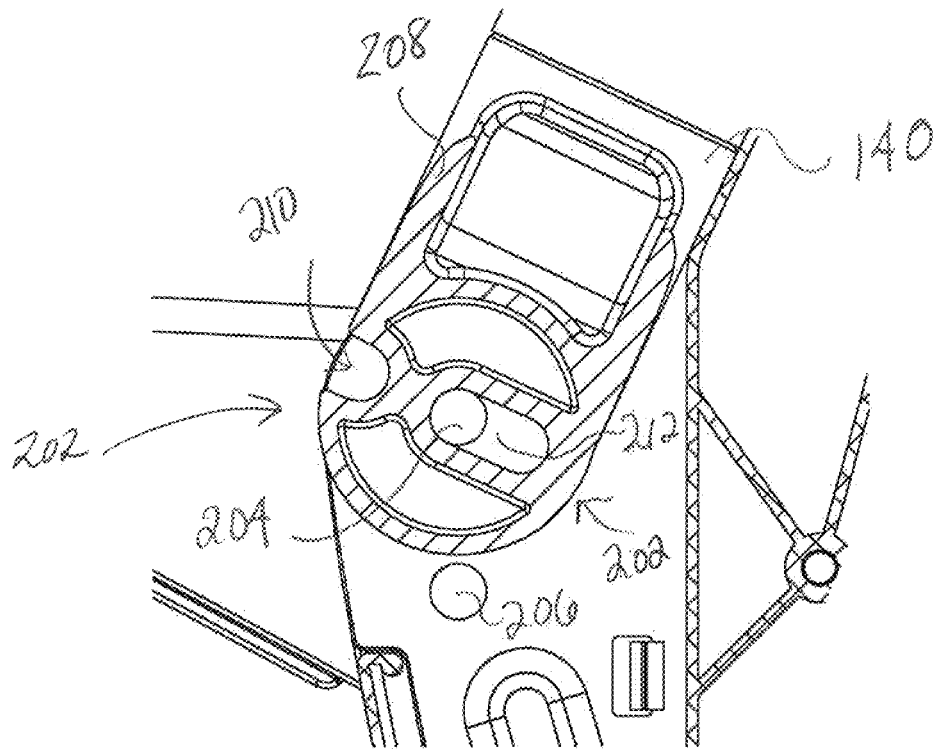

FIG. 15 depicts a front view and side view of elevating walker chair 100 with handle bar 140 in an extended position. FIG. 15 includes a cross-section taken through AA-AA. Cross-section AA-AA shows a handle bar pivot 202. The side view of elevating walker chair 100, identical to FIG. 2, is shown again for reference. An enlargement of section AC of FIG. 15 is shown in FIG. 17A. Section AC depicts handle bar pivot 202 when handle bar 140 is in an extended position.

FIG. 16 depicts a front view of elevating walker chair 100 with handle bar 140 in a folded position. FIG. 16 includes a cross-section taken through AB-AB. Cross-section AB-AB shows handle bar pivot 202 as configured when handle bar 140 is in a folded position. A side view of elevating walker chair 100 identical to FIG. 3 is shown again for reference. An enlargement of section AD of FIG. 16 is shown in FIG.

17B. Section AC depicts handle bar pivot 202 when handle bar 140 is in a folded position.

FIG. 17A depicts handle bar pivot 202 when handle bar 140 is extended. Handle bar pivot 202 may include a first pivot pin 204 and a second pivot pin 206, each extending from end block 126. A pivot element 208 is attached to or integral with handle bar 140. Pivot element 208 includes a pivot notch 210 and a pivot slot 212. When handle bar 140 is extended, first pivot pin 204 is positioned toward the outer portion of pivot slot 212 and second pivot pin 206 is in engaged in notch 210. If a force 214 is applied to handle bar 140 near handle bar pivot 202, the force will have a significant upward vector component, and cause pivot element 208 to also move upward, thereby repositioning pivot slot 212 so that first pivot pin 204 is toward an inner portion of pivot slot 212. Force 214 will also disengage second pivot pin from pivot notch 210. The resulting configuration is shown in FIG. 17B. Handle bar 140 will still pivot about first pivot pin 204, but is no longer locked in place by second pivot pin 206. This allows handle bar 140 to pivot toward the rear of elevating walker chair 100. With handle bars 140 folded upward or rearward in this manner, a user may position elevating walker chair closer to a table or counter, for example. If force 214 is applied further out along handle bar 140, i.e. away from an occupant, handle bar 140 will rotate about first pivot pin 204, without disengaging from pivot notch 210.

It is noted that a conventional latch or similar mechanism may be used in place of the pivot notch 210 and pivot slot 212 combination of pivot element 208.

Elevating walker chair 100 may have different types of seats 104. FIGS. 18-22 depict a swivel seat 302 in the form of a saddle with a broad rear section. Features of swivel seat 302 may also be used with other shaped seats.

Figure 18:
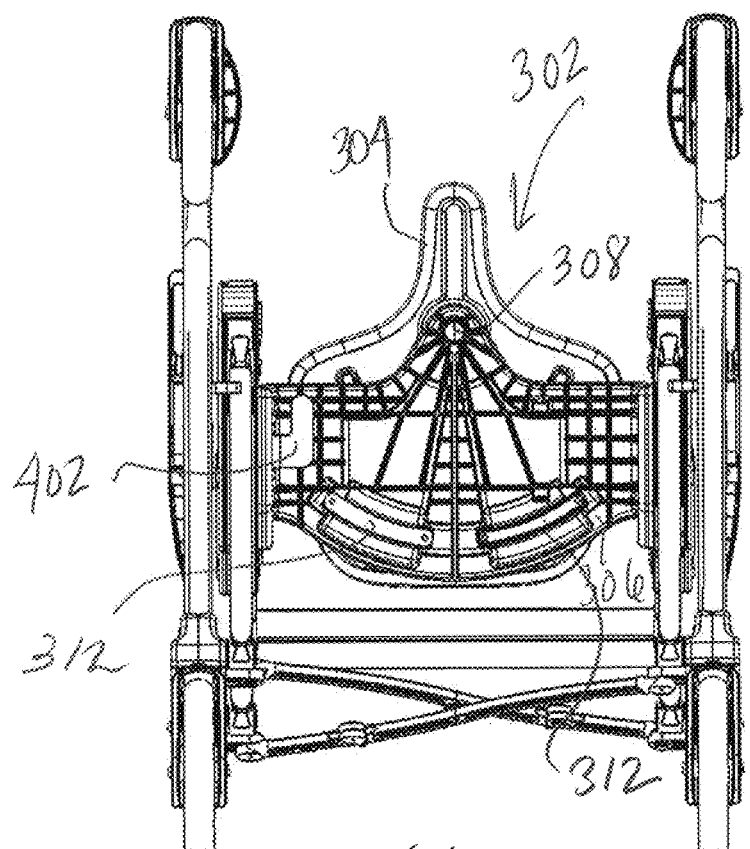
FIG. 18 is a bottom view of an elevating walker chair.
Figure 19:
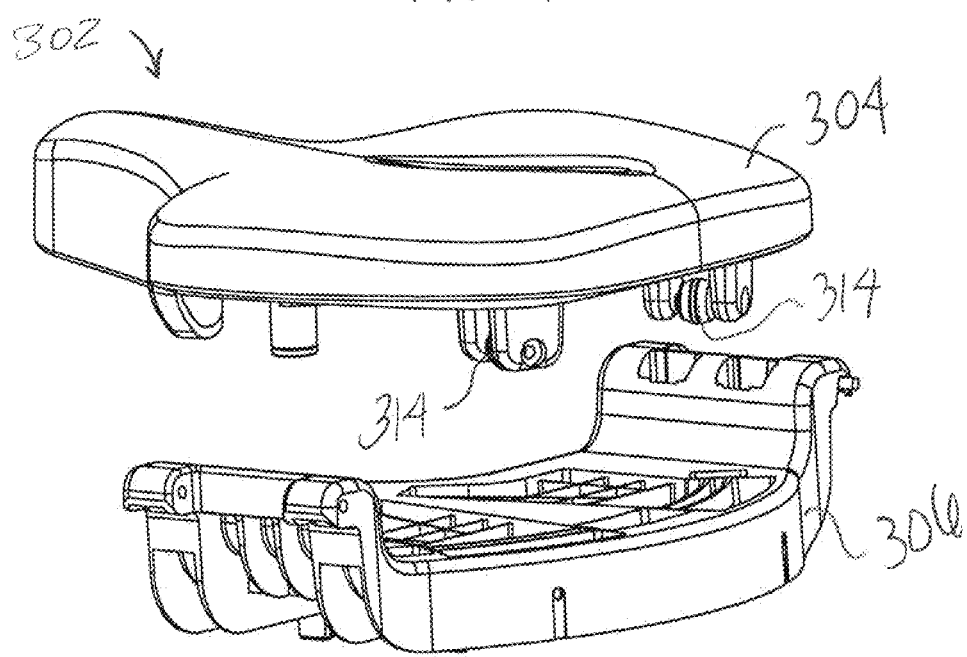
FIG. 19 depicts an exploded view of a swivel seat for an elevating walker chair.
Figure 20:
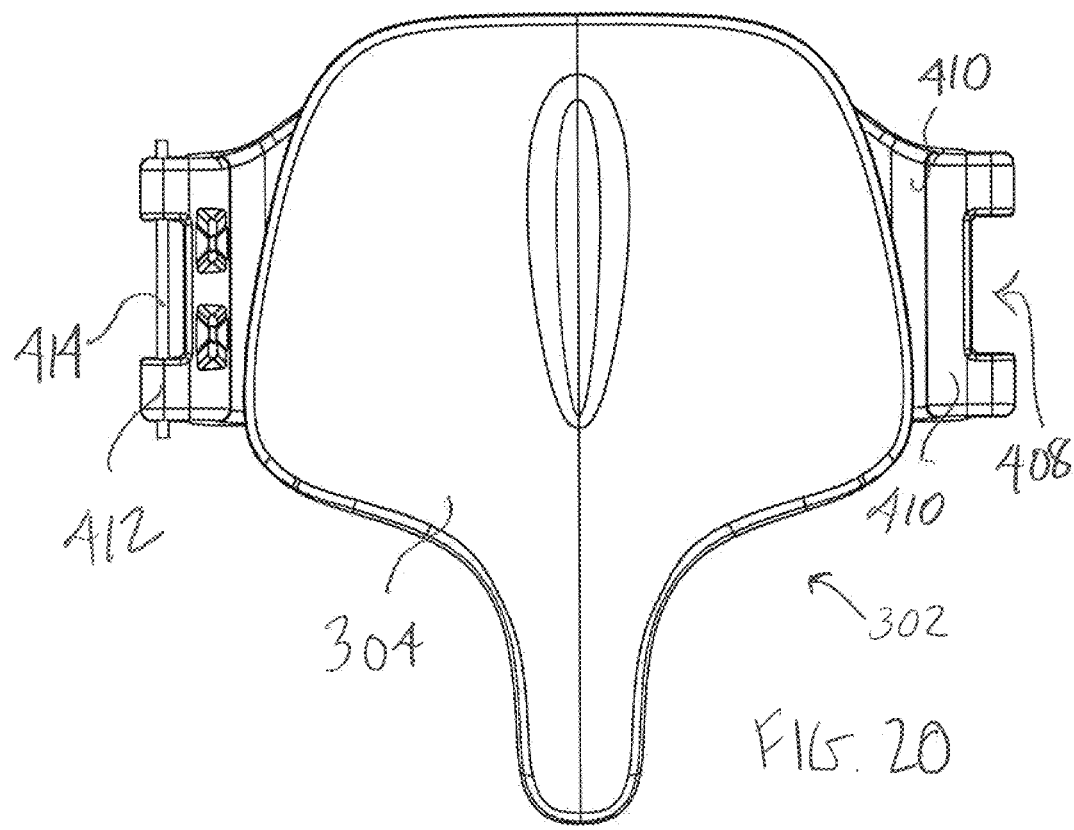
FIG. 20 depicts a top view of a swivel seat.
Figure 21:
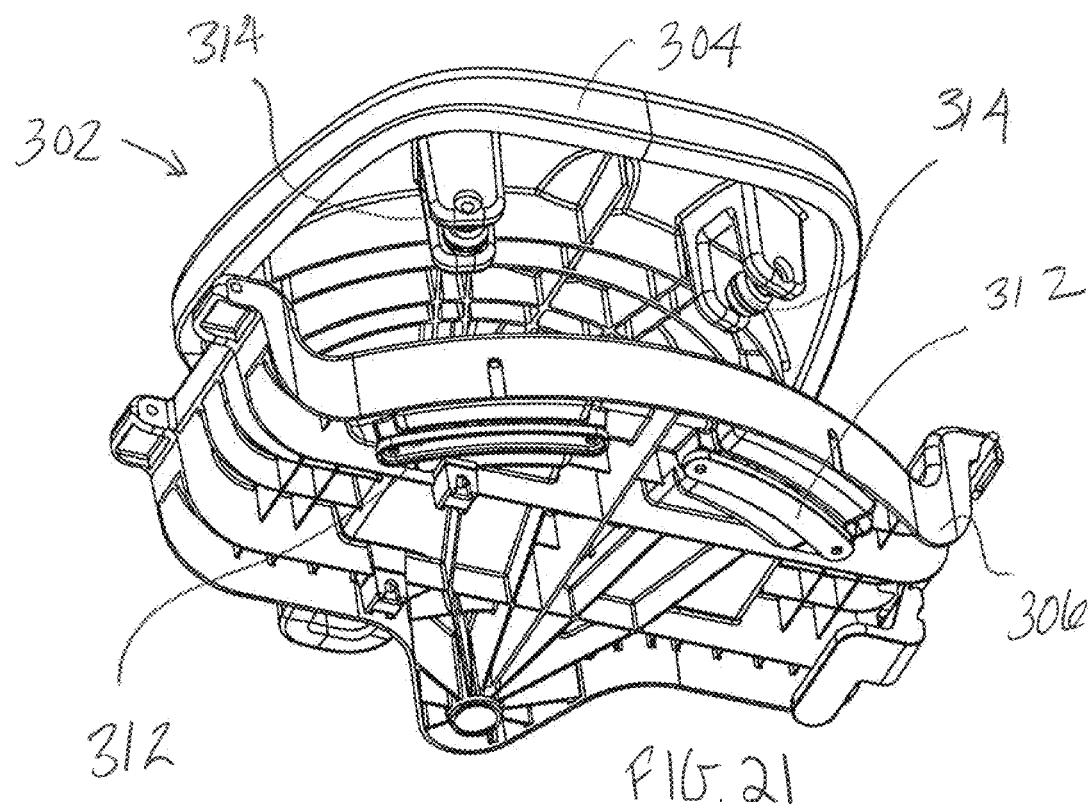
FIG. 21 depicts an exploded view showing detail of the underside of a swivel seat.

FIG. 18 is a bottom view of swivel seat 302. FIG. 19 shows an exploded view that includes top section 304 and bottom section 306, which are configured to connect to one another. FIG. 20 depicts a top view of swivel seat 302. FIG. 21 depicts an exploded view showing detail of the underside of swivel seat 302. FIG. 22 is a view from the underside of swivel seat 302 with a cross-section taken through AE-AE. Various structural flanges or components are pictured, which may not be necessary, depending on the material and dimensions of swivel seat 302 and its applications.

Swivel seat 302 pivots about seat pivot 308. Seat pivot 308 may comprise a hole with a post disposed within, or other pivot mechanism. Swivel seat 302 may have one or more roller apparatuses 310, primarily for additional structural support that may reduce the torque of the structure as compared to a swivel seat supported only at a single pivot. This potential reduction results from swivel seat 302 having a plurality of points or areas of contact.

Roller apparatuses 310 include curved tracks or openings 312 disposed at a radial distance from seat pivot 308 in bottom seat section 306. The center of the arc of each track 312 is seat pivot 308. Rollers 314 that are complementary to tracks 312, are disposed on top section 304. When top section 304 is engaged with bottom section 306, rollers 314 fit into tracks 312. The contact between rollers 314 and tracks 312 provides support for seat 302, while allowing seat 302 to freely swivel about seat pivot 308. The position of rollers 314 and tracks 312 may be reversed as to which is contained on top section 304 and bottom section 306. The length of tracks 312 may vary and may depend for example on the number of tracks incorporated into the seat, the weight of the seat and the weight range of the intended occupants.

Also visible in FIGS. 18 and 22 is a release lever 402 to disengage seat 302 (or other seat 104) so elevating walker chair 100 may be folded as designed to do. By "foldable" it is meant that elevating walker chair may be collapsible, which may include parts collapsing in manners other than folding. It is noted that swivel seat 302 may be used on other apparatuses in addition to an elevating walker chair.

FIGS. 23-30 depict an elevating walker chair 100 folding mechanism and shows elevating walker chair in various stages of the folding process.

Figure 23:
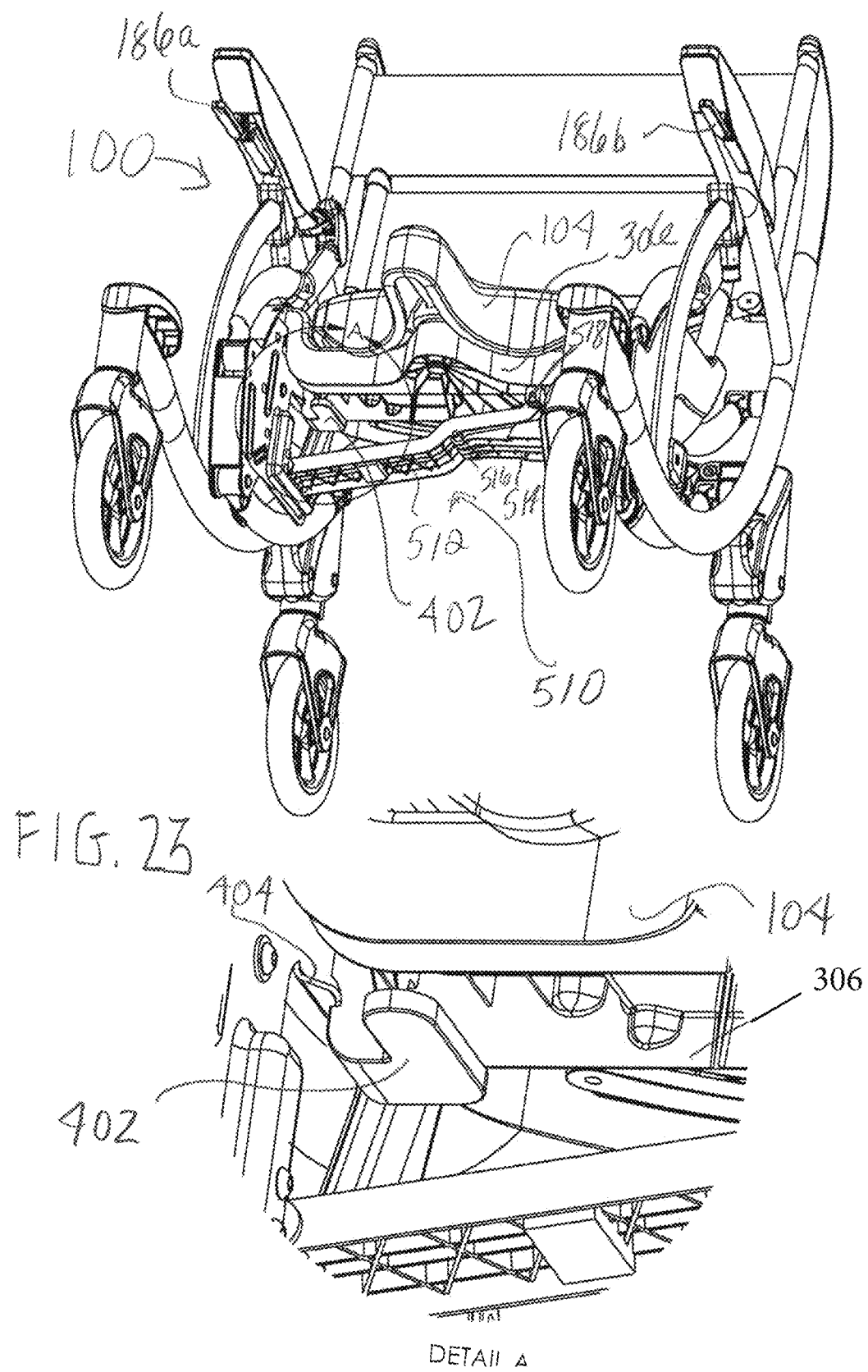
FIG. 23 shows an isometric view of an elevating walker chair, with an enlargement of a seat release lever portion.

FIG. 23 shows an isometric view of elevating walker chair 100, with an enlargement of section A. A lever 402 is attached to seat bottom section 306. FIG. 24 depicts a bottom view and front view of elevating walker chair 100, and a cross-sectional view taken through D-D. Lever 402 engages with a hook 404. Hook 404 is located on end block 126. Therefore, when lever 402 is engaged with hook 404, seat 104 is locked in place.

FIG. 25 depicts a bottom view and front view of elevating walker chair 100, and a cross-sectional view taken through G-G. Lever 402 is shown disengaged from hook 404 by rotation about lever pivot 406. It is noted that the location of the lever and hook could be reversed. Additionally, release lever 402 may be positioned elsewhere, provided that it functions as intended. Also, hook 404 may be on a component other than end block 126, depending on the configuration of elevating walker chair 100. For example, hook 404 may be located on a portion of frame 118. The latching mechanism should allow seat 104 to rotate when lever 402 is depressed, and be locked in place when it is engaged. Other seat latching mechanisms may be used, provided they accomplish this function and are compatible with other components of elevating walker chair 100.

Figure 26:
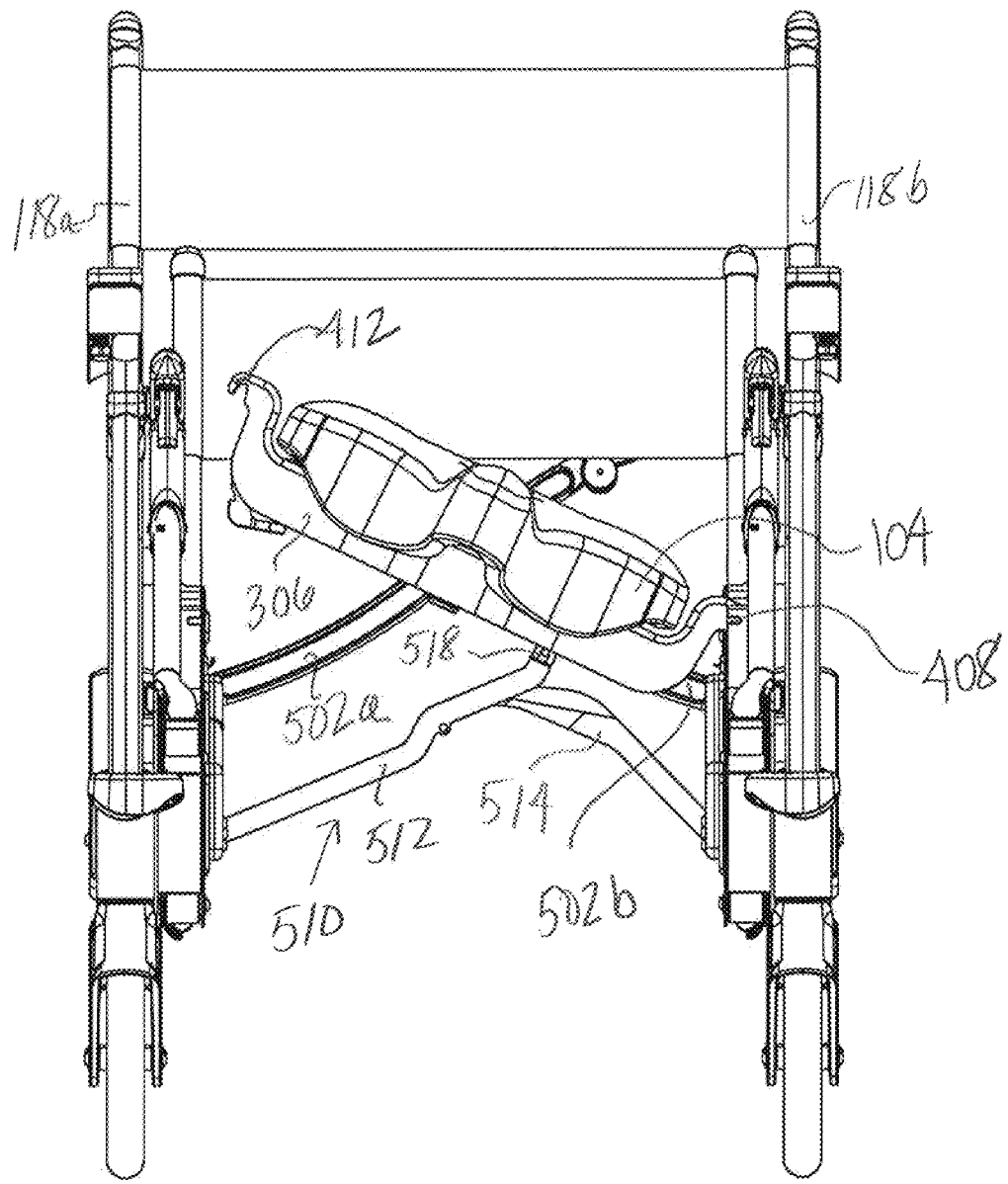
FIG. 26 shows a front view of a partially folded elevating walker chair.

FIG. 26 shows a front view of elevating walker chair 100 when seat 104 has been partially rotated about seat hinge 408, the location and portions of which are shown in FIG. 20. A seat hinge section 410 of seat hinge 408 engages with a complementary hinge section that may be attached, for example, to end block 126. On a side opposite to seat hinge 408, seat 104 has a seat catch 412 that engages with a bar 414. Bar 414 may be affixed to or integral with seat hook 414. When seat catch 412 is engaged with bar 414, seat 104 is supported in a horizontal or near horizontal position for use as a seat or user support for the standing or walking mode. Seat 104 may be stabilized by other stabilizing mechanisms, provided that they hold the seat in place when elevating walker chair 100 is in use, adequately support a user during sitting, standing and walking and do not interfere, i.e. are compatible, with other components and functions of elevating walker chair 100.

Figure 27:
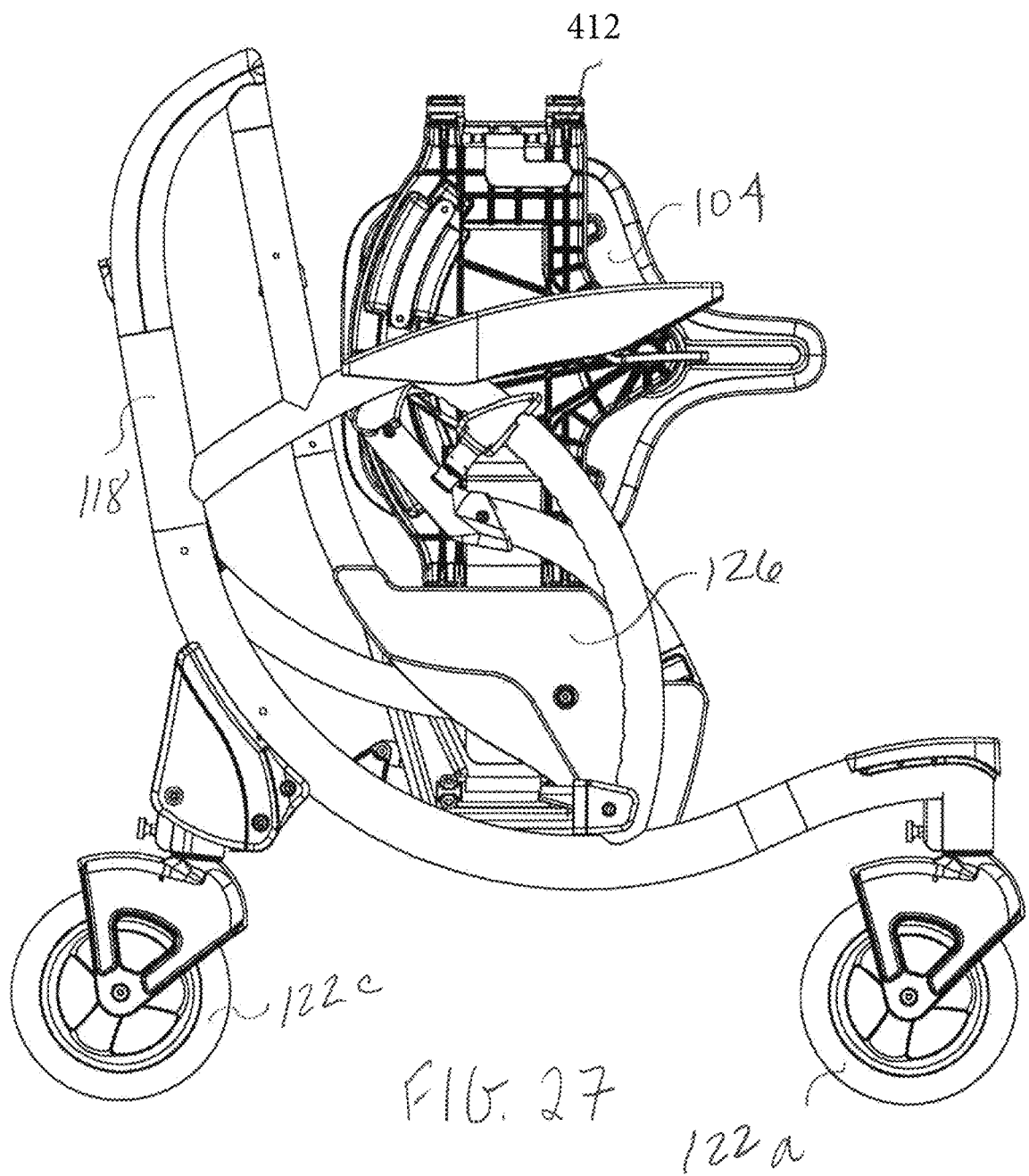
FIG. 27 depicts a side view of a folded elevating walker chair.
Figure 28:
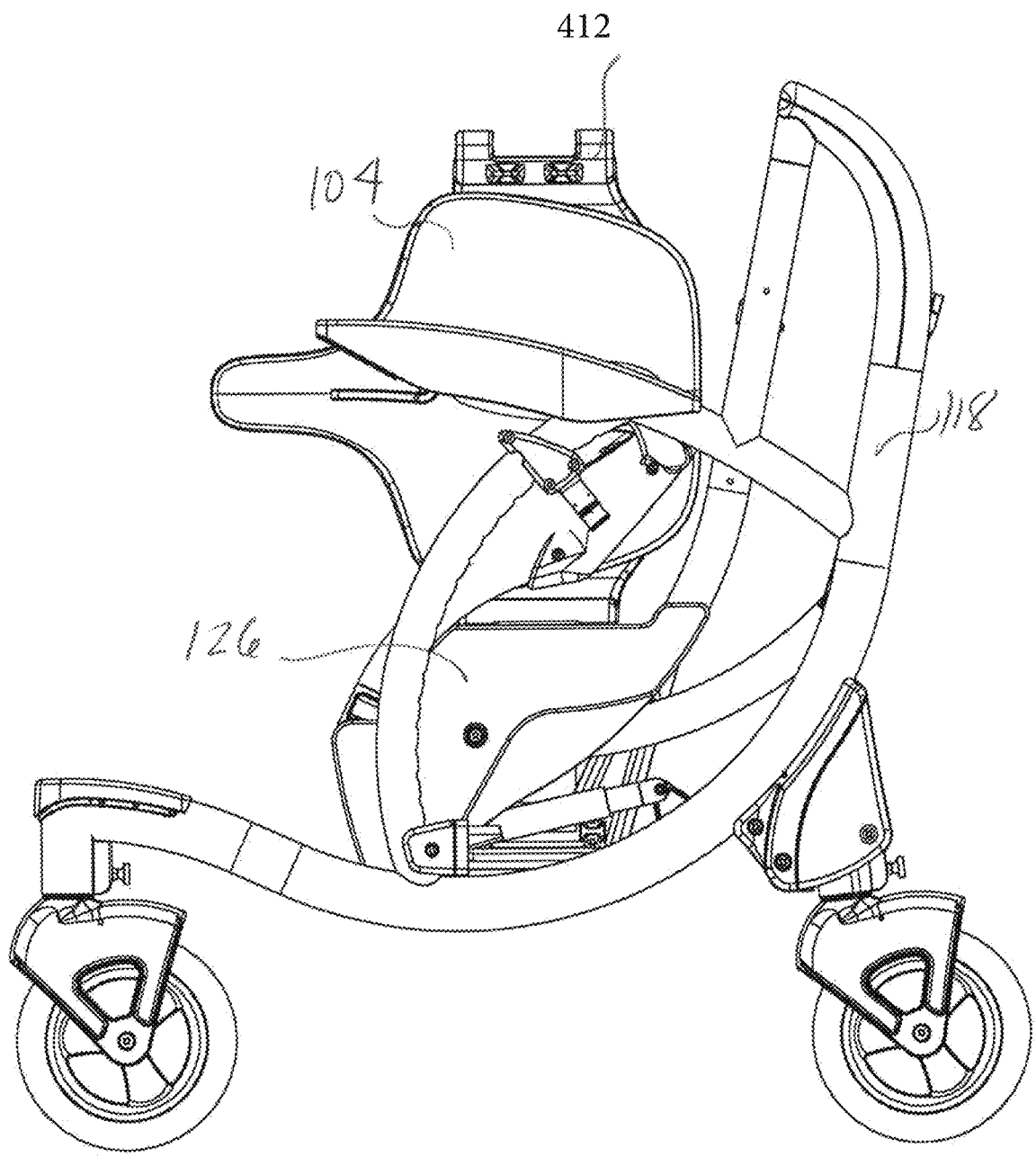
FIG. 28 depicts a side view of a folded elevating walker chair from a side opposite to the view of FIG. 27.
Figure 29:
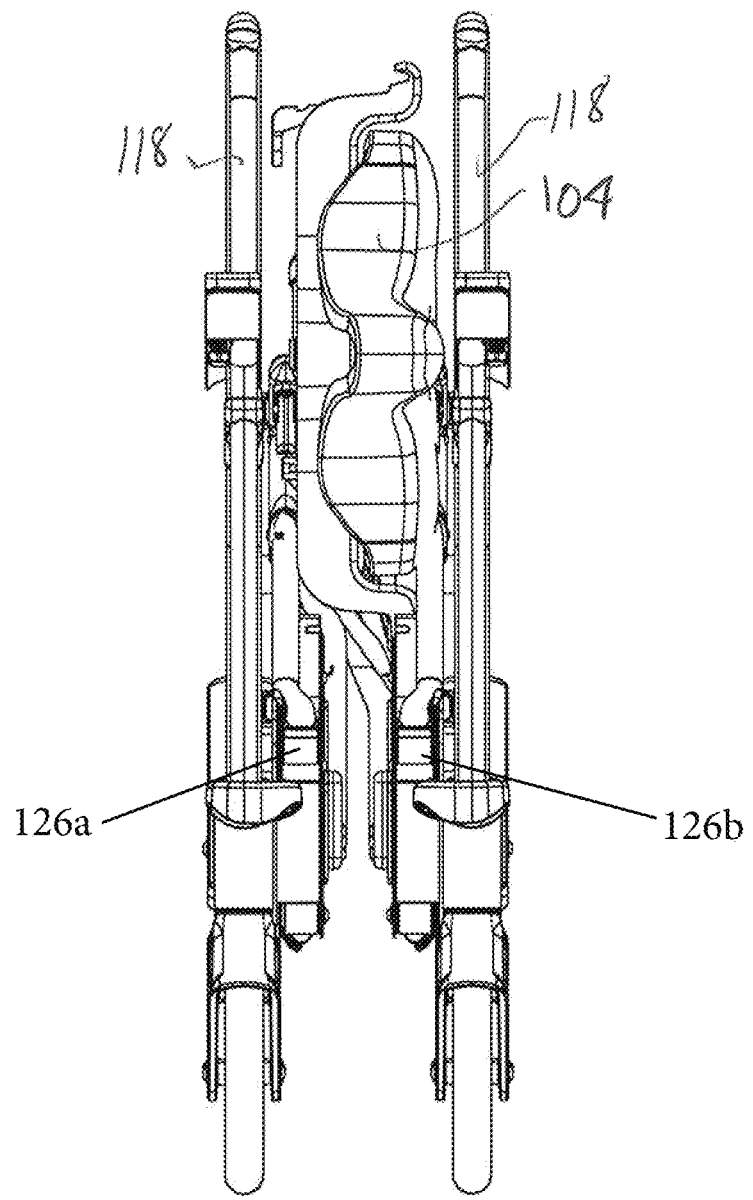
FIG. 29 is a front view of a folded elevating walker chair.
Figure 30:
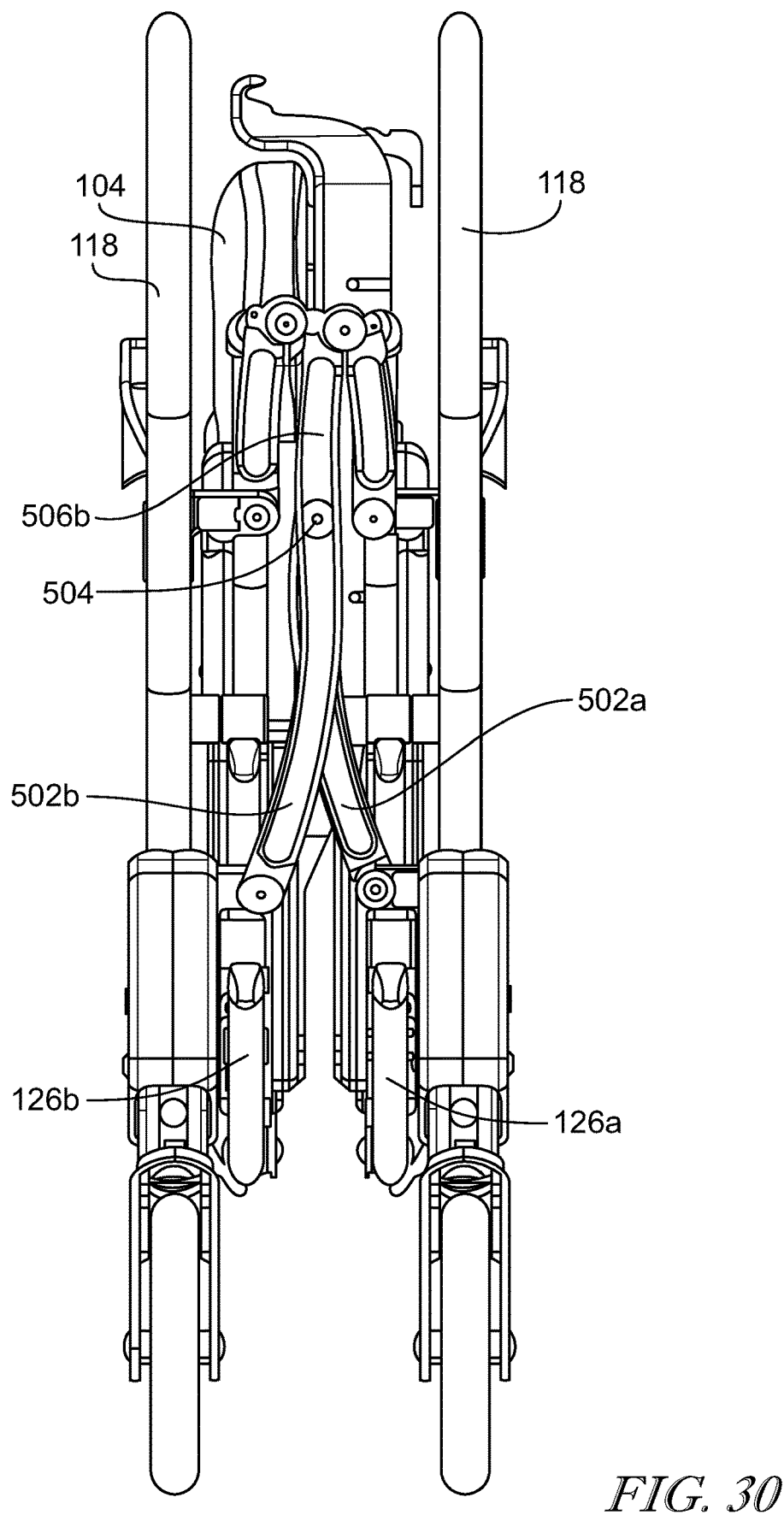
FIG. 30 is a rear view of a folded elevating walker chair.

FIGS. 27-30 depict elevating walker chair in a folded configuration. Elevating walker chair 100 may be locked in a folded position. In the illustrative embodiment shown, elevating walker chair 100 is preferably folded when in its lowest (sitting) position. FIGS. 27 and 28 are opposing side views of a folded elevating walker chair 100. FIG. 27 shows the view from the side on which bar 414 is located. FIG. 28 depicts the view from the side on which seat hinge 408 is located. As can be seen by FIGS. 27, 28, seat 104 rotates about a relatively horizontal axis so the sitting surface of seat 104 is substantially vertical. This allows frame 118 to be collapsed so that end blocks 126a, 126b can be moved toward each other, as shown by folded elevating walker chair 100 front view and rear view in FIGS. 29, 30, respectively.

Figure 31:
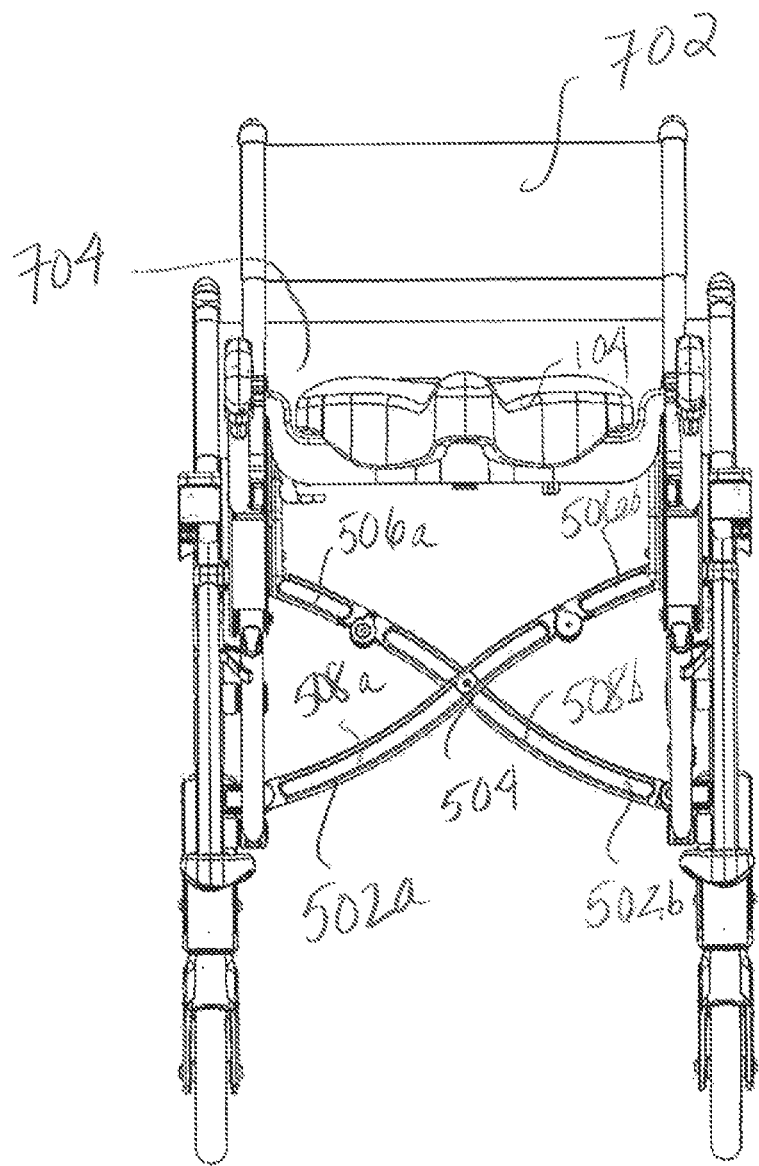
FIG. 31 depicts a front view of an elevating walker chair showing the cross arms of a bracing and folding mechanism.

FIG. 31 shows cross arms 502a, 502b, which are part of the elevating walker chair folding mechanism. Cross arms

502a, 502b pivot at cross arm pivot 504. Each of cross arms 502a, 502b is made up of two hinged sections 506a,b, 508a,b. The "hinge" connecting the hinged sections may be any rotating mechanism that allows cross arms 502a, 502b to fold as desired. The "hinge" may be a conventional pivot, for example. Cross arm sections 506a, 506b, 508a, 508b are attached to frame 118, and may function to keep end blocks 126 square with each other when unfolded in normal use. As cross arms 502a, 502b rotate toward alignment with one another in a scissor fashion, right and left sides of frame 118 come toward each other. Cross arm sections 506a, 506b fold downward with respect to cross arm sections 508a, 508b to allow right and left sections of frame 118 to come as close together as possible. Cross arms 502a, 502b may nest within each other for compactness.

Returning to FIGS. 23, FIG. 24, section D-D and FIG. 25, section G-G, a foldable seat support 510 is visible. Foldable seat support 510 comprises two section 512, 514 hinged in a scissor fashion at a first seat support pivot 516. First seat support section 512 is also hinged to seat bottom section 306 at a second seat support pivot 518. As the right and left sides of frame 118 come together, seat support section 514 folds downward and comes together with seat support section 512. Seat support sections 512, 514 nest with one another and fold around seat bottom section 306. Second seat pivot 518 allows foldable seat support to support seat 104 in the folded configuration.

As can be see, for example, in the illustrative embodiment in FIGS. 27, 28, elevating walker chair 100 may be configured when folded so that seat release-catch 412 is positioned so a user may grip the apparatus to provide walking support. Wheels 122a, 122b, 122c, 122d remain positioned on the ground so will allow elevating walker chair to roll as a user walks while gripping seat hinge section 410. Different "handle" configurations may be incorporated into elevating walker chair 100. In this embodiment, elevating walker chair 100 is balanced in the folded position to allow it to be used as a walking support. This means that when a user shifts their weight to handle 410 for support, elevating walker chair 100 will remain positioned on the ground without tipping or with less of a likelihood of tipping. This is made possible by having wheels 122a, 122b, 122c, 122d level with one another, and sufficiently spaced apart. Additionally, handle 410 may be positioned to inhibit a user's weight from tipping elevating walker chair 100.

The configuration described may allow elevating walker chair 100 to be folded without the user bending, or with the user minimally bending. However, other folding mechanisms may be incorporated into elevating walker chair 100.

Figure 32:
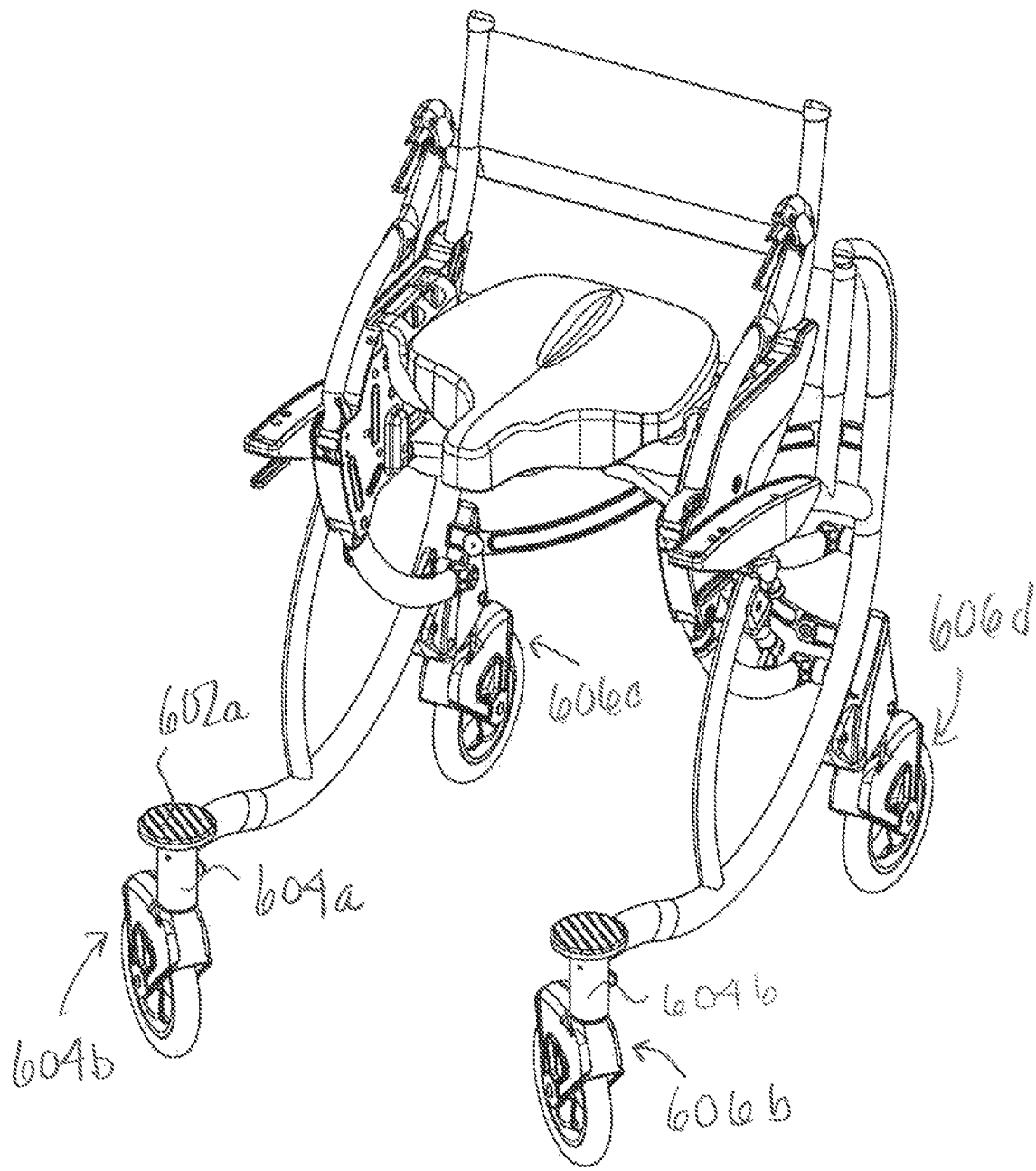
FIG. 32 is an isometric view of an elevating walker chair showing caster-steering footplates.
Figure 33:
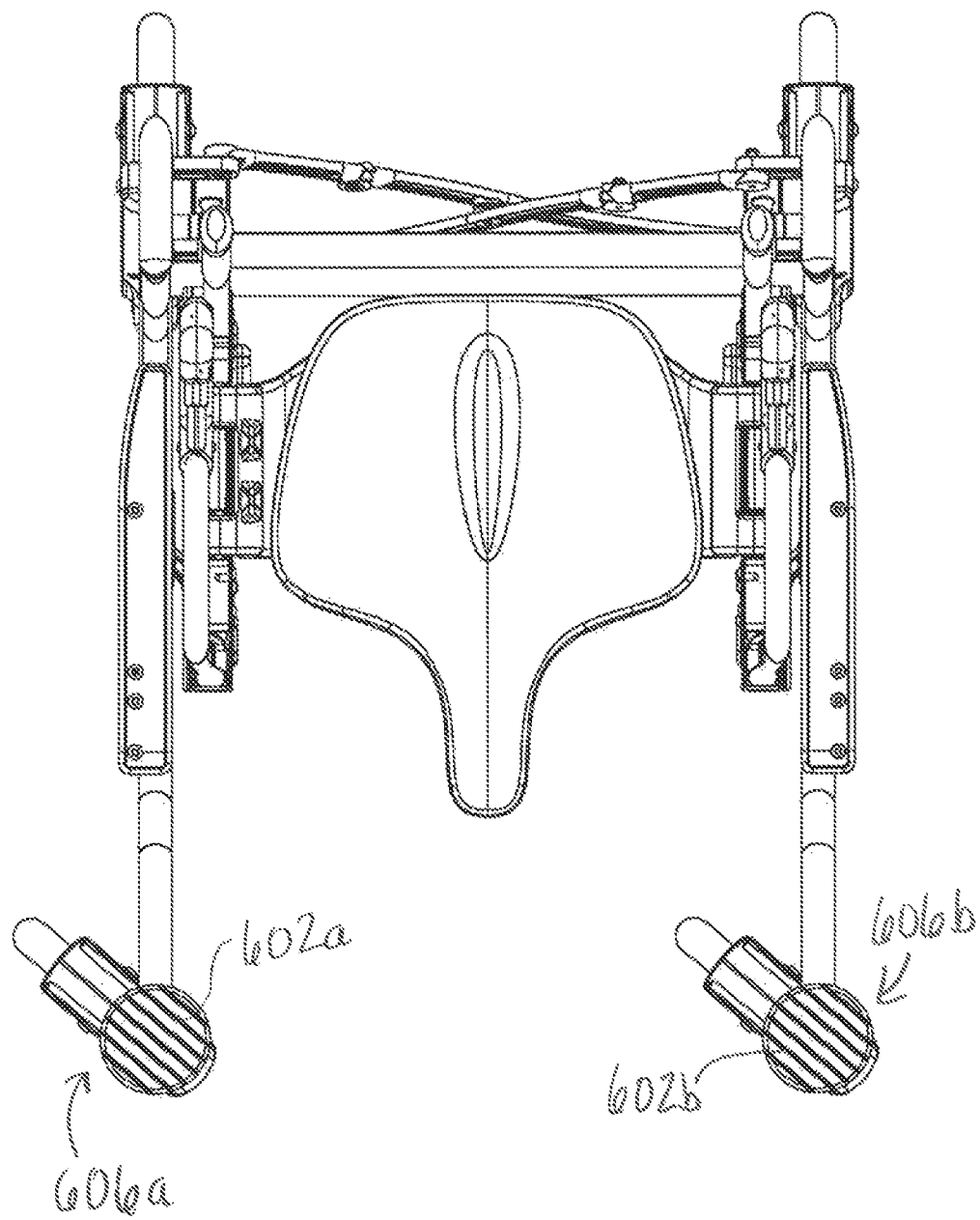
FIG. 33 is a top view of an elevating walker chair showing caster-steering footplates in an angled position.
Figure 34:
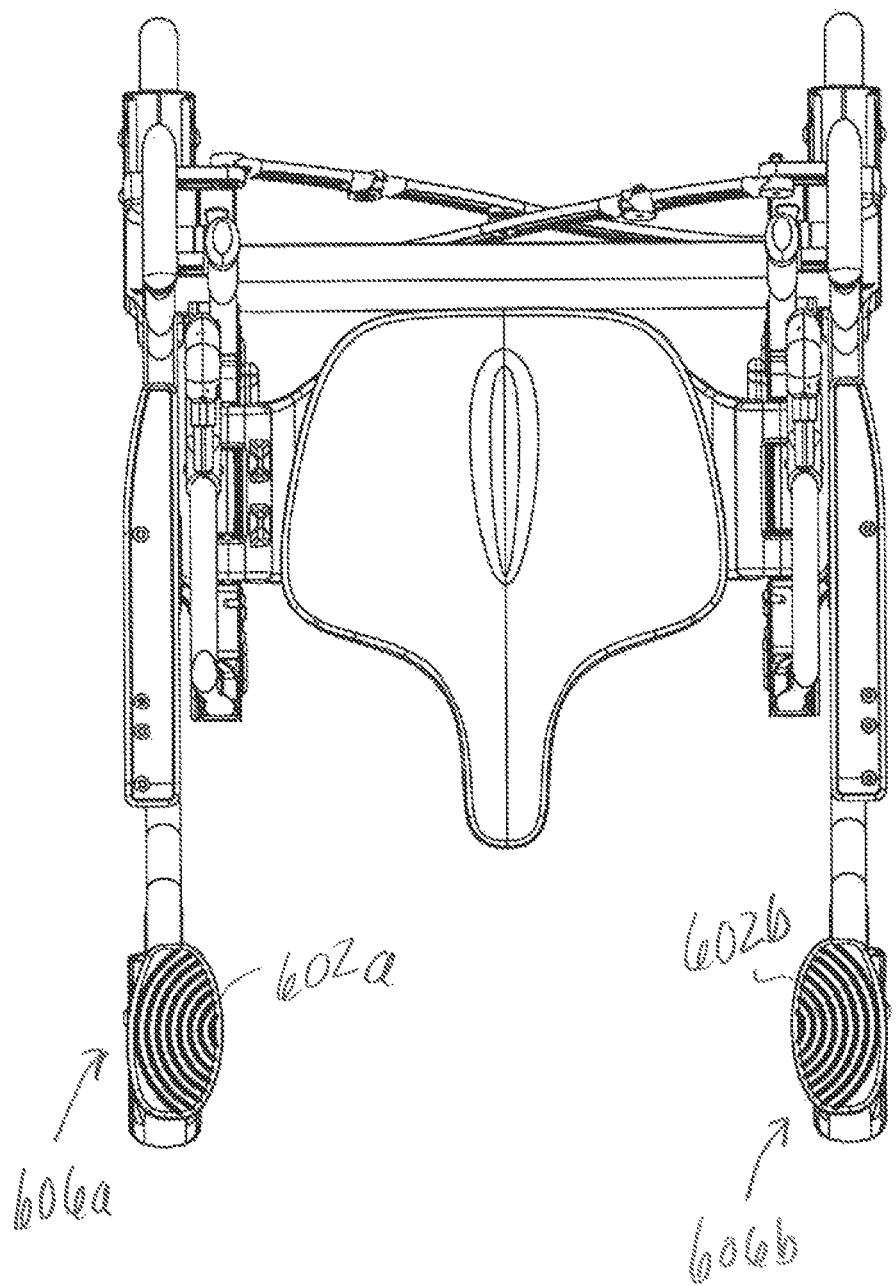
FIG. 34 is a top view of an elevating walker chair showing caster-steering footplates in a forward position.

FIGS. 32-34 show caster steering footplates 602a, 602b. Footplates 602a, 602b are fixedly associated with axles 604a, 604b of front casters 606a, 606b. Thus, rotation of footplates 602a, 602b rotates front casters 606a, 606b. FIGS. 32 and 33 are an isometric view and top view, respectively, of elevating walker chair 100 showing footplates 602a, 602b angled away from a direct forward position. As can be seen in FIG. 32, casters 606a, 606b are also rotated. FIG. 34 is a top view of elevating walker chair 100 showing footplates 602a, 602b and casters 606a, 606b in a forward orientation. These particular footplates are shown as oval. Footplates 602a, 602b enable an occupant to steer elevating walker chair 100 by rotating casters 606a, 606b with their feet to cause the chair to follow a desired path. Footplates preferably have sufficient friction to engage a user's foot/shoe to allow for steering.

Figure 35A:
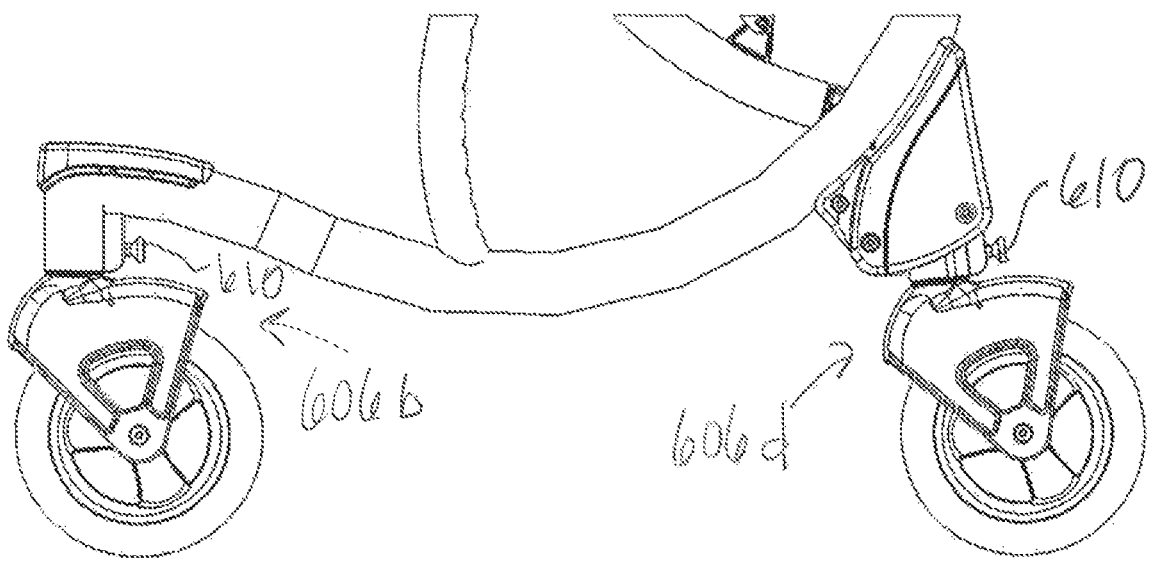
FIGS. 35A, 35B show casters in a non-extended and vertically extended configuration, respectively.
Figure 35B:
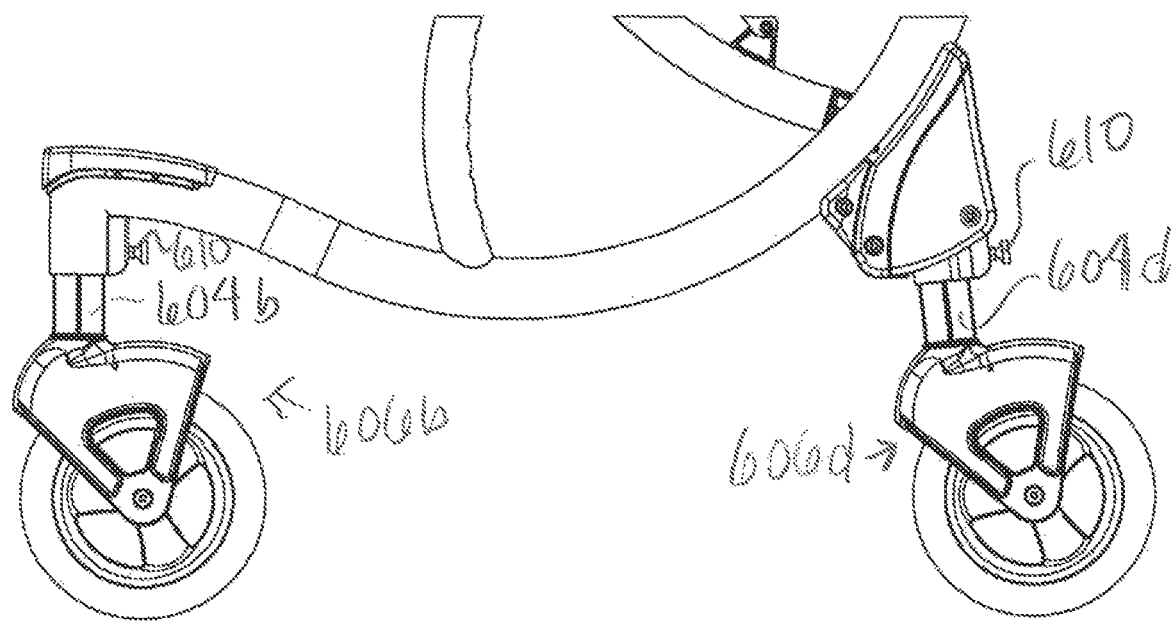

FIGS. 35A, 35B show casters 606b, 606a in a non-extended and vertically extended configuration, respectively. Axles 604a, 604d may be extended from sleeves 608a, 608b, respectively. A release pin 610 is provided to secure casters 606b, 606a at a selected extension. Other mechanisms may be employed to lengthen the distance of casters 606 from the bottom of sleeve 608.

Figure 36:
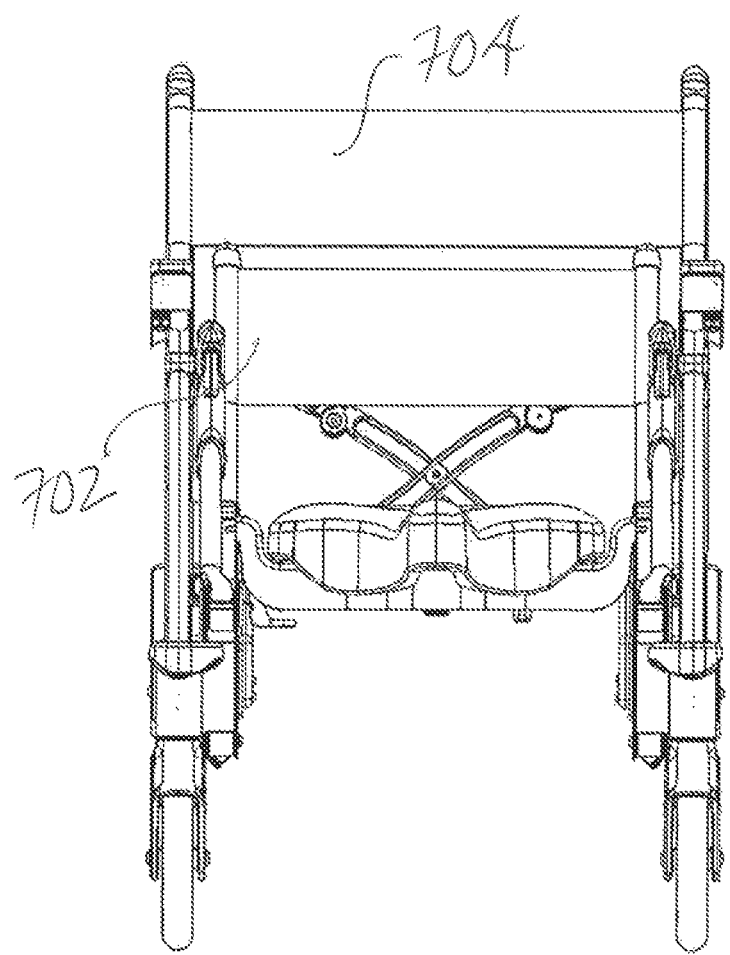
FIG. 36 depicts a front view of an elevating walker chair having two backrests.

Turning to FIG. 36, viewed in conjunction with FIG. 31, an embodiment is shown wherein elevating walker chair 100 may have two backrests 702, 704. Backrest 702 is affixed to end block 126 so rises and falls as seat 104 is moved up and down. Backrest 702 could be fixed to any other component that rises and falls with seat 104, provided the configuration is compatible with the design and functioning of elevating walker chair 100. Backrest 704 may be attached to frame 118 so remains stationary with respect to the height from ground level when seat 104 is lowered or raised.

Figure 39:
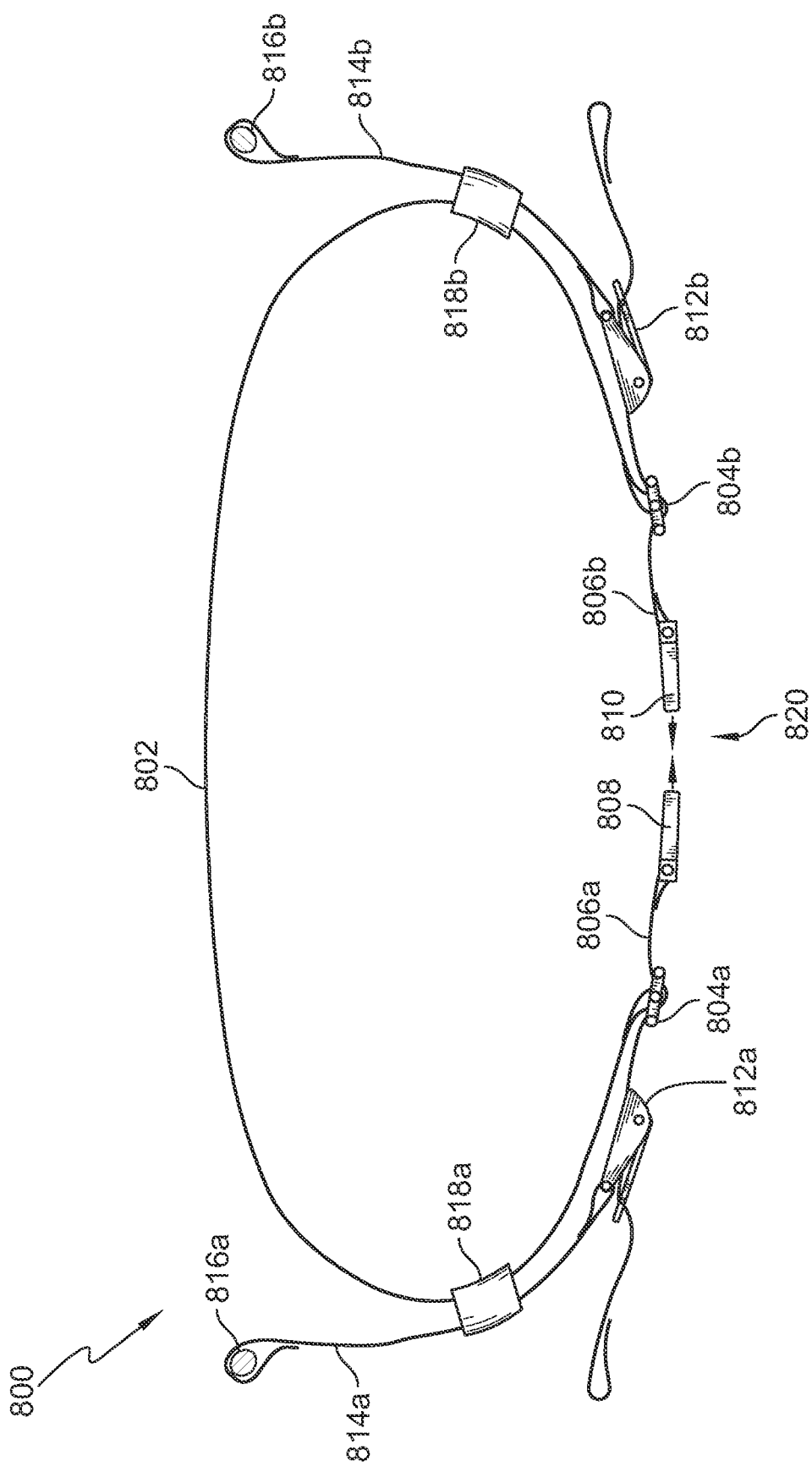
FIG. 39 depicts a top view of a seatbelt for use with an elevating walker chair.
Figure 40:
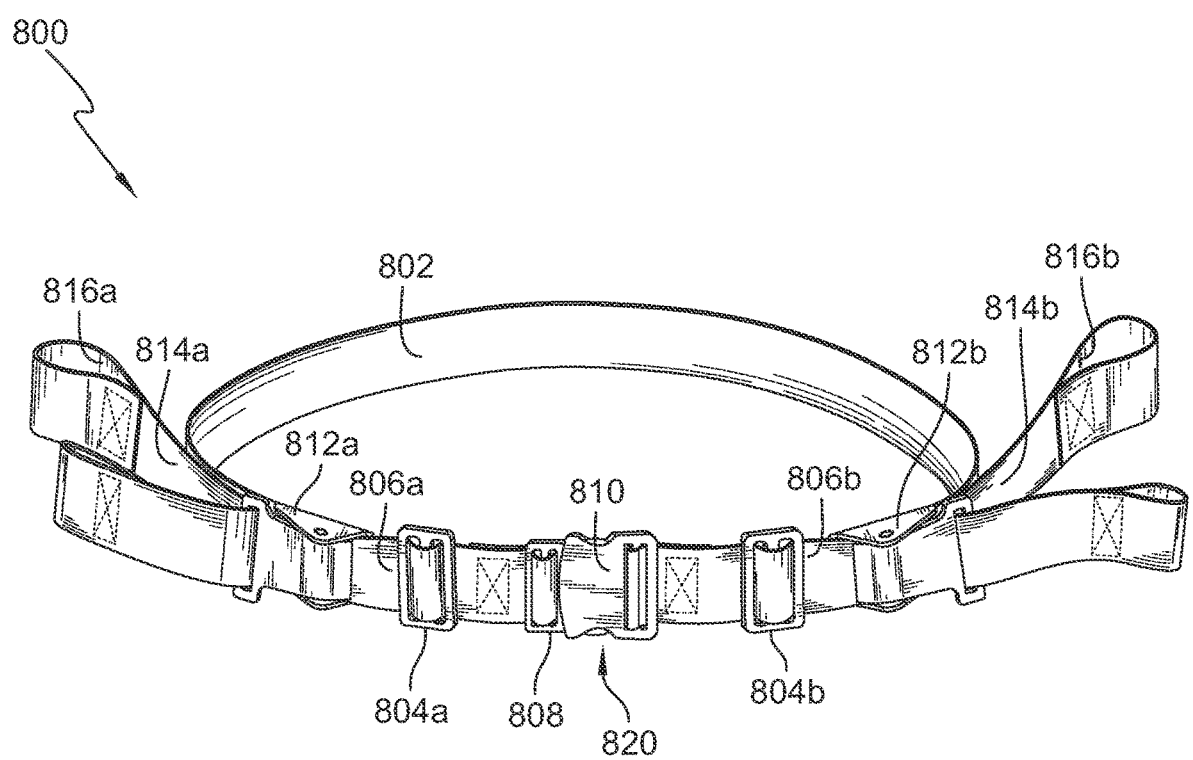
FIG. 40 depicts a perspective view of a seatbelt for use with an elevating walker chair.

FIGS. 39 and 40 depict a top view and isometric view, respectively, of a seatbelt 800 that may be used with elevating walker chair 100. Seatbelt 800 has a stretchable belt portion 802 that may be, for example, elastic or other stretchable fabric or material. Stretchable belt portion 802 is positioned around a user's back and extends to the front of a user where it is attached at each end to a stretchable belt portion adjustment device 804a, 804b. Stretchable belt portion adjustment devices 804a, 804b may be used to fit stretchable belt portion 802 to a user. The elastic characteristic of this portion of seatbelt 800 may allow a user to more easily and comfortably transition between elevating walker chair modes, such as sitting, standing/walking and barstool mode, for example, by reducing or eliminating unwanted slackness and drooping of a conventional seatbelt, that could occur when sliding from the front portion of a seat, back to sit on the rear portion.

Alternatively, or in addition to stretchable material and adjustment devices, seatbelt 800 may employ retractors. The seat belt material would extend out of the retractor. A conventional seat belt retractor includes a mechanism configured to lock up to secure a user in place, for example on sudden movement or impact.

To form a full loop around a user, seatbelt 800 has front belt portions 806a, 806b. Front belt portion 806a is connected to a belt buckle portion 808, and front belt portion 806b is connected to a complementary belt buckle portion 810. Together, belt buckle portion 808 and complementary belt buckle portion 810 form a belt buckle 820, which secures seatbelt 800 around a user. Belt buckle 820 may be centrally located in front of a user for ease of buckling.

Front belt portions 806a, 806b are also threaded through stretchable belt portion adjustment device 804a, 804b. Stretchable belt portion adjustment device 804a, 804b may be, for example, tri-glide buckle-strap adjuster devices. Stretchable belt portions 806a, 806b may be of materials having various degrees of stretchability, depending for example, on the application of the seatbelt, size of the user and other user needs.

Front belt portions 806a, 806b are further threaded through belt adjustments 812a, 812b. Anchoring portions 814a, 814b are attached to belt adjustment device 812a, 812b. Anchoring portions 814a, 814b are secured to elevating walker chair 100 at frame 118 at frame attachments 816a, 816b. Anchoring portions 814a, 814b may be made of a non-stretch webbing, that may be semi-rigid, for example, or other material with the necessary durability and ability to secure a user in position as needed, while providing any desired flexibility for user needs and comfort. Loops 818a, 818b may be provided to optionally maintain anchoring portions 814a, 814b in place.

Figure 41A:
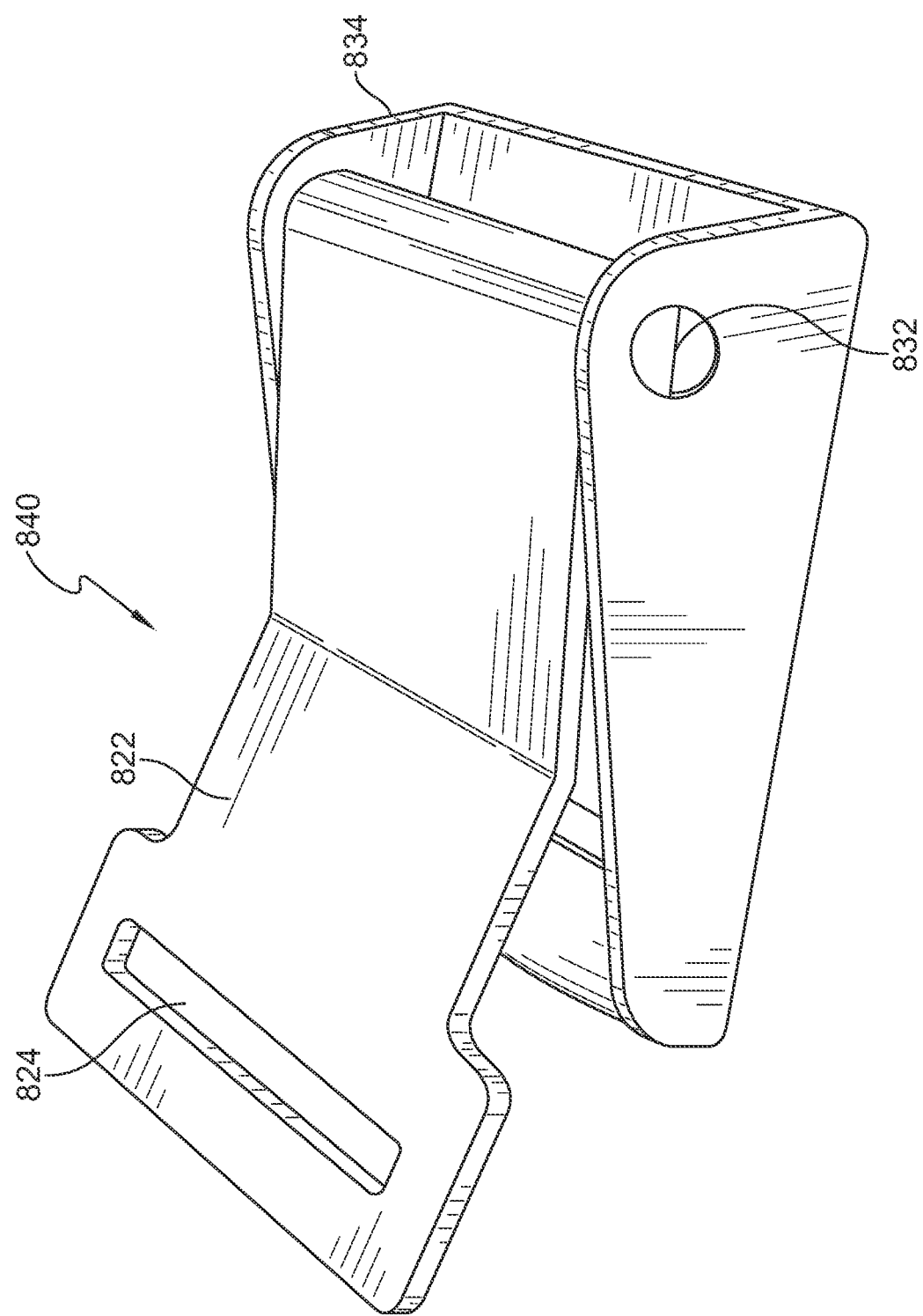
Figure 41B:
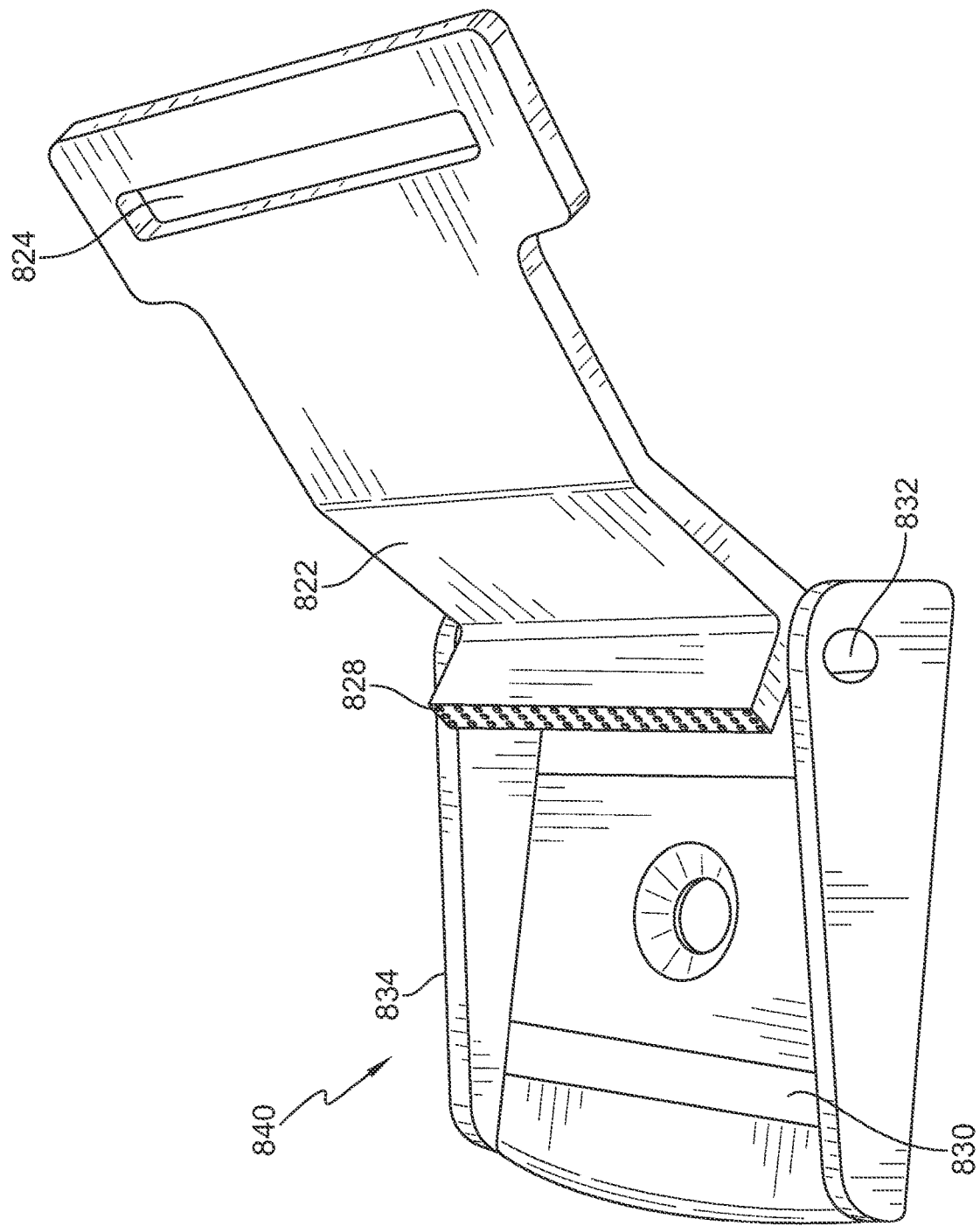

FIGS. 41A-C depict a belt adjustment device 812 in the form of a cam buckle 840. FIG. 41A shows cam buckle 840 in a closed position. FIG. 41B depicts cam buckle 840 in an open position. FIG. 41C shows cam buckle 840 with a portion of a strap, such as front belt portion 806, threaded through it. Each cam buckle 840a, 840b is attached to an anchoring portion 814a, 814b at cam buckle base slot 830.

Cam buckle 840 has a cam buckle base 834 and a cam buckle lever 822 hingedly attached thereto at cam buckle pivot 832. Each cam buckle 840 is positioned with its hinged end toward the front of elevating walker chair 100. On each side, right and left, of seat belt 800, front belt portion 806 is threaded between cam buckle base 834 and cam buckle lever 822, while cam buckle lever 822 is rotated to an open position. Front belt portion 806 is then thread through cam buckle lever slot 824. This leaves a portion of front belt portion 806 extending rearward from cam buckle 840. This portion shall be referred to as a belt adjustment portion 826. A user can pull forward on a belt adjustment portion 826 to rotate cam buckle lever 822 away from cam buckle base 834, thus allowing front belt portion 806 to slide between cam buckle base 834 and cam buckle lever 822 to either tighten or loosen seatbelt 800. By pulling rearward on a belt adjustment portion, the selected belt size is locked into place. The illustrative cam buckle 840 shown in FIG. 41B has teeth 828 to secure front belt portion 806 in place and inhibit slippage. Other means to inhibit slippage may be implemented, such as sufficient pressure or non-slip material. Cam buckle lever 822 is configured so when rotated to a closed position, it will remain or be forced closed when front belt portion 806 is pulled forward at the hinged end of cam buckle 802, such as when a user is leaning forward. Front belt portions 806 may be non-stretchable or may be of materials having various degrees of stretchability, depending for example, on the application of the seatbelt and other user needs.

It is noted that seatbelt 800 may be used on other apparatuses so the anchoring mechanisms may vary. Additionally, adjustment mechanism may vary.

Various embodiments of the elevating walker chair and its components have been described. The invention is not limited to the specific embodiments or combinations of elements disclosed. The invention may include different combinations of the elements, omission of some elements or the replacement of elements by the equivalents of such structures. For example, the elevating walker chair may be foldable or non-foldable While illustrative embodiments have been described, additional advantages and modifications will occur to those skilled in the art. Therefore, the invention in its broader aspects is not limited to specific details shown and described herein. Accordingly, it is intended that the invention not be limited to the specific illustrative embodiments, but be interpreted within the full spirit and scope of the appended claims and their equivalents.

The invention claimed is:

1. An elevating walker chair comprising:
a frame having four wheels;
a seat attached to the frame;
an adjustable lifting mechanism attached to the seat comprising:
a parallelogram structure having four pivotally connected links, the parallelogram connected to the frame at at least two of the four pivots and on opposite sides of the seat; and
a spring pivotably extending from a first link of the parallelogram to an adjustable termination point on a second link of the parallelogram to form a lifting triangle, wherein the spring termination point is displaced from a first pivot of the parallelogram; and
a height adjustment mechanism comprising:
an arcuate height adjustment strut;
a wall of the height adjustment strut having a series of holes; and
a height adjustment pin associated with a parallelogram link and selectively insertable into the holes to lock in a selected height of the seat.

2. The elevating walker chair of claim 1, further comprising a lifting power adjustment mechanism having an arced slot having notches configured to engage a spring pin at a selected notch, the radius of the slot matching a pivoting radius of an opposing end of the spring when the spring is fully extended.

3. The elevating walker chair of claim 2 further comprising an auxiliary compression spring to facilitate adjustment of the spring pin in the slot.

4. The elevating walker chair of claim 1 wherein the seat is in the form of a saddle.

5. The elevating walker chair of claim 1 further comprising a maximum height adjustment mechanism having:
an interior cross-web extending longitudinally within the arcuate height adjustment strut;
the wall of the arcuate height adjustment strut having the series of holes;
the cross-web having a series of holes aligned with the height adjustment strut wall holes;
a maximum height limiter pin;
a compression spring disposed around the maximum height limiter pin;
wherein the maximum height limiter pin extends through a selected height adjustment strut wall hole and the aligned cross-web hole to lock in a maximum height of the seat; and
wherein the maximum height limiter pin can be withdrawn from the selected holes and inserted into other selected holes to adjust the maximum height of the seat.

6. The elevating walker chair of claim 1 wherein the height adjustment mechanism further comprises:
a compression spring disposed around the height adjustment pin.

7. The elevating walker chair of claim 6 further comprising:
a height lock safety mechanism configured so that the friction between the height adjustment pin and the height adjustment strut wall holes keeps the height adjustment pin in place when the seat is unoccupied; and
the friction is reduced when the seat is equipoised or near equipoised by the lifting mechanism, thus freeing the height adjustment to be retracted.

8. The elevating walker chair of claim 1 further comprising a folding mechanism having:
a hinge connecting the seat at an outer seat side to the frame, configured to allow the seat to rotate toward a vertical position;
two cross arms pivotably connected at a cross arm pivot, each cross arm connected to the frame;
each of the two cross arms comprising two hinged sections rotatably connected to one another;
the two cross arms configured to rotate toward alignment with one another in a scissor fashion, as opposing sides of the frame come toward each other;
a seat support having two sections hinged in a scissor fashion at a first seat support pivot; and the seat support further hinged to the seat on the seat bottom at a second seat support pivot.

9. The elevating walker chair of claim 1 having rotatable handle bars wherein the handle bars rotate from a forward position to a rear position.

10. The elevating walker chair of claim 1 wherein the seat swivels, and the swivel seat comprises:
a top seat section and a bottom seat section;
a seat pivot in the form of a pole extending from the underside of the seat;
one or more weight-supporting roller apparatuses;
each of the one or more roller apparatuses having a curved track disposed at a radial distance from the seat pivot in either the top seat section or the bottom seat section, and having the seat pivot as the center of the track pivot; and
rollers complementary to the tracks disposed on either the top section or bottom section, wherein the rollers fit into the track.

11. The elevating walker chair of claim 1 wherein the front wheels are part of caster apparatuses and the elevating walker chair further comprises:
footplates fixedly associated with axles of the casters, the footplates configured to steer the elevating walker chair.

12. The elevating walker chair of claim 1 configured to provide clearance for a user's legs to allow the user to use a natural gait to propel the elevating walker chair.

13. The elevating walker chair of claim 1, wherein the adjustable termination point on the second link is variably offset from the second link of the parallelogram.

14. An elevating walker chair comprising:
a frame having four wheels;
a seat attached to the frame;
an adjustable lifting mechanism attached to the seat comprising:
    a parallelogram structure having four pivotally connected links, the parallelogram connected to the frame at least two of the four pivots; and
    a spring pivotably extending from a first link of the parallelogram to an adjustable termination point on a second link of the parallelogram to form a lifting triangle, wherein the spring termination point is displaced from a first pivot of the parallelogram;
    a lifting power adjustment mechanism configured to adjust the position of the spring termination point with respect to the first pivot;
a height adjustment mechanism comprising:
    a height adjustment strut;
    a wall of the height adjustment strut having a series of holes;
    a height adjustment pin associated with a parallelogram link and selectively insertable into the holes to lock in a selected height of the seat;
a maximum height adjustment mechanism having:
    the height adjustment strut having an interior cross-web extending longitudinally within the height adjustment strut;
    the wall of the height adjustment strut having the series of holes;
    the cross-web having a series of holes aligned with the height adjustment strut wall holes;
    a maximum height limiter pin;
    wherein the maximum height limiter pin extends through a selected height adjustment strut wall hole and the aligned cross-web hole to lock in a maximum height of the seat; and
    wherein the maximum height limiter pin can be withdrawn from the selected holes and inserted into other selected holes to adjust the maximum height of the seat.

15. An elevating walker chair comprising:
a frame having four wheels;
a seat attached to the frame;
an adjustable lifting mechanism attached to the seat comprising:
    a parallelogram structure having four pivotally connected links, the parallelogram connected to the frame at at least two of the four pivots; and
    a spring pivotably extending from a first link of the parallelogram to an adjustable termination point on a second link of the parallelogram to form a lifting triangle, wherein the spring termination point is displaced from a first pivot of the parallelogram;
    a lifting power adjustment mechanism configured to adjust the position of the spring termination point with respect to the first pivot;
a height adjustment mechanism comprising:
    a height adjustment strut;
    a wall of the height adjustment strut having a series of holes;
    a height adjustment pin associated with a parallelogram link and selectively insertable into the holes to lock in a selected height of the seat;
a folding mechanism having:
    a hinge connecting the seat at an outer seat side to the frame, configured to allow the seat to rotate toward a vertical position;
    two cross arms pivotably connected at a cross arm pivot, each cross arm connected at each end to the frame;
    each of the two cross arms comprising two hinged sections rotatably connected to one another;
    the two cross arms configured to rotate toward alignment with one another in a scissor fashion, as opposing sides of the frame come toward each other and the two hinged sections of the two cross arms fold downward at the hinges;
    a seat support having two sections hinged in a scissor fashion at a first seat support pivot; and
    the seat support further hinged to the seat on the seat bottom at a second seat support pivot.

16. An elevating walker chair comprising:
a frame having four wheels;
a seat attached to the frame;
an adjustable lifting mechanism attached to the seat comprising:
    a parallelogram structure having four pivotally connected links, the parallelogram connected to the frame at at least two of the four pivots; and
    a spring pivotably extending from a first link of the parallelogram to an adjustable termination point on a second link of the parallelogram to form a lifting triangle, wherein the spring termination point is displaced from a first pivot of the parallelogram;
    a lifting power adjustment mechanism configured to adjust the position of the spring termination point with respect to the first pivot; and
a height adjustment mechanism comprising:
    a height adjustment strut;
    a wall of the height adjustment strut having a series of holes;

a height adjustment pin associated with a parallelogram link and selectively insertable into the holes to lock in a selected height of the seat; and wherein the seat swivels, and the swivel seat comprises:
a top seat section and a bottom seat section;
a seat pivot in the form of a pole extending from the underside of the seat;
one or more weight-supporting roller apparatuses;
each of the one or more roller apparatuses having a curved track disposed at a radial distance from the seat pivot in either the top seat section or the bottom seat section, and having the seat pivot as the center of the track pivot; and
rollers complementary to the tracks disposed on either the top section or bottom section, wherein the rollers fit into the track.

* * * * *